United States Patent
Usagawa

(10) Patent No.: US 9,383,329 B2
(45) Date of Patent: Jul. 5, 2016

(54) GAS SENSOR AND A METHOD OF MANUFACTURING THE SAME

(75) Inventor: Toshiyuki Usagawa, Saitama (JP)

(73) Assignee: Hitachi, Ltd., Tokyo (JP)

( * ) Notice: Subject to any disclaimer, the term of this patent is extended or adjusted under 35 U.S.C. 154(b) by 428 days.

(21) Appl. No.: 13/810,516

(22) PCT Filed: Aug. 9, 2011

(86) PCT No.: PCT/JP2011/068202
§ 371 (c)(1),
(2), (4) Date: Jan. 16, 2013

(87) PCT Pub. No.: WO2012/043071
PCT Pub. Date: Apr. 5, 2012

(65) Prior Publication Data
US 2013/0186178 A1    Jul. 25, 2013

(30) Foreign Application Priority Data
Sep. 29, 2010    (JP) ................................. 2010-218983

(51) Int. Cl.
*G01N 27/06*    (2006.01)
*B82Y 15/00*    (2011.01)
(Continued)

(52) U.S. Cl.
CPC ................ *G01N 27/06* (2013.01); *B82Y 15/00* (2013.01); *B82Y 30/00* (2013.01); *G01N 27/4141* (2013.01); *G01N 27/4146* (2013.01)

(58) Field of Classification Search
CPC ..................................................... G01N 27/06
USPC ...................................................... 73/31.06
See application file for complete search history.

(56) References Cited

U.S. PATENT DOCUMENTS

2012/0217550 A1*   8/2012   Usagawa ........... G01N 27/4141
                                                                             257/253
2013/0313569 A1*   11/2013   Usagawa ................ H01L 29/78
                                                                              257/77

FOREIGN PATENT DOCUMENTS

JP    2009-254522 A    11/2009
JP    2009-300297    *   12/2009
JP    2009-300297 A    12/2009
(Continued)

OTHER PUBLICATIONS

Isolde Simon et al., Micromachined metal, oxide gas sensors: opportunities to improve sensor performance , Germany Institute of Physical and Theoretical Chemistry, Sensors and actuators (2001).*

(Continued)

*Primary Examiner* — Hezron E Williams
*Assistant Examiner* — Hoang Nguyen
(74) *Attorney, Agent, or Firm* — Mattingly & Malur, PC

(57) ABSTRACT

The gas sensor has a substrate, a gate insulating film arranged on the substrate, and a gate electrode arranged on the gate insulating film, wherein the gate electrode comprises a metal oxide mixture film produced by mixing an oxygen-doped amorphous metal that contains oxygen with crystals of an oxide of the metal and a platinum film formed on the metal oxide mixture film, the platinum film is composed of multiple platinum crystal grains and grain boundary regions that are present between the platinum crystal grains, the grain boundary regions are filled with a metal oxide mixture, and each of the platinum crystal grains is surrounded by the metal oxide mixture.

14 Claims, 17 Drawing Sheets

(51) Int. Cl.
*G01N 27/414* (2006.01)
*B82Y 30/00* (2011.01)

(56) References Cited

FOREIGN PATENT DOCUMENTS

| JP | 2010-008371 | A | | 1/2010 |
|---|---|---|---|---|
| JP | 2010-164411 | | * | 7/2010 |
| JP | 2010-164411 | A | | 7/2010 |
| WO | 2011/055605 | A1 | | 5/2011 |

OTHER PUBLICATIONS

Japanese Office Action received in Japanese Application No. 2010-218983 dated Apr. 8, 2014.
Shimizu et al. Applied Physics, 2001, vol. 70, No. 4, pp. 423-427.
Simon et al., "Micromachined metal oxide gas sensors: opportunities to improve sensor performance", Sensor and Actuators B, 2001, vol. 73, pp. 1-26.
Suzuki et al., "A Micromachined Gas Sensor based on a Catalytic Thick Film/SnO2 Thin Film Bilayer and Thin Film Heater, Part 1: CH4 Sensing" The 10th Int. Meeting, Chemical Sensors, Jul. 11-14, 2004, 3B02, Tsukuba, Japan.
Winquist et al., Modified palladium metal-oxide-semiconductor structures with increased ammonia gas sensitivity, Appl. Phys. Lett., Nov. 1, 1983, vol. 43, No. 9, pp. 839-841.
Dobos et al., "Performance of Carbon Monoxide-Sensitive MOSFET's with Metal-Oxide Semiconductor Gates", IEEE Transactions on Electron Devices, Jul. 1985, vol. ED-32, No. 7, pp. 1165-1169.
Dannetun et al., NO dissociation on polycrystalline palladium studied with a Pd-metal-oxide-semiconductor structure, J. Appl. Phys., Aug. 1, 1989, vol. 66, No. 3, pp. 1397-1402.
Lundstrom et al., "Catalytic Metals and Field-effect Devices—a Useful Combination", Sensors and Actuators, B1, 1990 pp. 15-20.
Usagawa et al., "Developments and Lifetime Evaluations for Low Power Si-MOSFET Hydrogen Gas Sensors", Fuel Cell, 2009, vol. 8, No. 3, pp. 86-96.
Usagawa, "A novel Pt-Ti-O gate Si-MISFETs hydrogen gas sensor", Chemical Sensors, Sep. 2, 2010, vol. 26, Supplement B, pp. 91 to 93.
Usagawa et al., "Air-Annealing Effects for Pt/Ti Gate Si-Metal-Oxide-Semiconductor Field-Effect Transistors Hydrogen Gas Sensor", Applied Physics Express, Mar. 19, 2010, vol. 3, pp. 047201-1-047201-3.
Usagawa et al., "Air-aneealing effects for Pt/Ti gate Si-MOSFETs hydrogen gas sensor", Chemical Sensors, Mar. 29, 2010, vol. 26, Supplement A, pp. 49 to 51.
Usagawa et al., "Device characteristics for Pt-Ti-O gate Si-MISFETs hydrogen gas sensors", Sensors and Actuaters B, Jun. 21, 2011.

* cited by examiner (a)

AIR ANNEALING AT 800°C FOR 30 min (b) SCHEMATIC CROSS SECTION BEFORE AIR ANNEALING (a) Pt DOMINANT RATIO (b) CAPACITOR DOMINANT RATIO (c) RESISTOR DOMINANT RATIO (a)

(b)

(a)

(b)

(c)

(a)

(b)

(a)

(b)

(c)

(a)

(b)

GAS SENSOR AND A METHOD OF MANUFACTURING THE SAME

TECHNICAL FIELD

The present invention concerns a gas sensor formed over a semiconductor substrate and a method of manufacturing the same and it particularly relates to a gas sensor having high reliability and high sensitivity provided over an Si semiconductor and a method of manufacturing the same.

BACKGROUND ART

In the latter half of 1970 years, research and development of manufacturing gas sensors by using Si-semiconductor processes in the rising period were taken place vigorously but they were declined except for ISFET used in live blood analysis. This was attributable mainly to that since the gas sensors were operated at high temperature (about 450° C.) in most cases crack or defoliation occurred in the thin film and long-term stability could not be achieved. The problem of peeling and cracking of the thin films was caused since the gas sensors had small heat capacity and poor thermal shock for the sake of the thin film, as well as that the process mainly includes dissolving fine grains in a solvent, and coating and sintering them in which no sufficient adhesive property between the fine grains and the substrate or the electrode can be ensured (for example, refer to Yasuhiro Shimizu, Makoto Egashira, Applied Physics, Vol. 70, No. 4, pp. 423 to 427, 2001 (Non-Patent Literature 1)). However, the technique of micro electro mechanical systems (MEMS) has been started for application to the development of the gas sensors about in the latter half of 1990 years and research and development therefor have become active again as a tramp for the low consumption power (for example, refer to I. Simon, et al., Sensors and Actuators B Vol. 73, pp. 1 to 26, 2001 (Non-Patent Literature 2), and T. Suzuki, et al. "10th Int. Meeting Chemical Sensors, 3B02, Jul. 11 to 14, 2004, Tsukuba, Japan" (Non-Patent Literature 3).

Most of current gas sensors adopt a catalytic combustion type, a metal-oxide semiconductor type, a gas thermal conduction type, and a solid electrolyte type. However, if various types of gas sensors can be achieved based on the Si-MOSFET technique (silicon semiconductor and integrated technique thereof), since a sensor sensitive portion can be formed of a hyper thin film and Si lithography can be utilized, it may be excepted that this can bring about a revolution in the field of the gas sensors while taking advantageous features of the Si semiconductor technique such as possibility of providing micro miniaturization, weight reduction, low consumption power, codeless operation (battery operation), portability, network adaptability, and mass production at low cost.

Actually, Si-MOSFET gas sensors for detecting $NH_3$, CO, $CH_4$, and NO gases by making the Pt gate thin film into a porous structure have been proposed though at a laboratory scale (Non-Patent Literatures 4, 5, 6). The principle of the sensor is that Pt small crystals are formed with an air gap therebetween over a gate insulating film and, when a gas molecule is adsorbed on Pt, a work function changes to shift the Vth of MOSs through the capacitance between the Pt small crystals.

An Si-MOSFET hydrogen gas sensor using a platinum film comprising a thin film at a thickness of about 30 to 45 nm for a gate electrode does not respond to ammonia, ethane, methanol, etc. except for a hydrogen gas. However, gas selectivity is different in the Si-MOSFET hydrogen gas sensor using a hyper thin platinum film (down to 6 nm) for a gate electrode (for example, refer to Sensors and Actuators B, Vol, pp. 15 to 20, 1990 (Non-Patent Literature 7). That is, according to their study, since the platinum thin film is not deposited uniformly over the gate insulating film and formed in a stripe shape, an air gap region with no platinum is present on the surface of the gate insulating film, and gas sensors capable of detecting also ammonia, ethane, methanol, etc. other than the hydrogen gas have been manufactured by utilizing the structure. It can be said that this is a gas sensor of positively utilizing the nature that the platinum film has poor adhesive property and tends to cause film peeling on the gate insulating film. The response mechanism of a gas sensor is as shown below as discussed in the literature (Non-Patent Literature 7) and other reference documents.

That is, ammonia gas or the like is deposited to the platinum surface formed in a stripe shape to change the surface potential $\phi_s$ on the platinum surface. In this case, the threshold value Vth changes, in principle, depending on static capacitance between the gap region with no platinum and the platinum small crystal at the surface of the gate insulating film and a static capacitance between the gap region with no platinum and the channel formed in the semiconductor substrate (Si substrate). However, also in the gas sensor using the hyper thin film (down to 6 nm) of the platinum, the problem of the reliability such as peeling of the platinum film has not yet been solved and the sensor still involves a problem and it is difficult to be put to practical use.

The Si-MOSFET hydrogen gas sensor using platinum as the gate electrode cannot be put to commercial product, because the adhesion property between the insulating film comprising, for example, silicon oxide and a semiconductor film comprising, for example, silicon or gallium arsenide (GaAs), etc. is poor and long-term reliability cannot be ensured. The problem of peeling of the platinum film is an extremely important problem also in view of the practical use and the ensurance of the working life in the gas sensor in which the gate electrode portion is exposed to an atmospheric air.

Further, partial film peeling is caused in the fabrication process of the FET manufacturing steps, and a technique of stably bonding Pt directly on the gate insulating film has not yet been established in practical production steps. Peeling of Pt film results in a problem of contamination to process apparatus due to the Pt film exfoliated in the manufacturing steps also in view of the manufacturing method, and a technique of avoiding the contamination had been established by inserting a barrier metal such as Ti, Mo, and W between Pt and an oxide such as $SiO_2$ or a semiconductor such as Si or GaAs thereby maintaining the adhesion in a case of using Pt in the field of electronic devices using Si, GaAs or the like. Pt is a noble metal and tends to become more stable when Pt is agglomerated per se than in a state of bonding with oxygen or other constituent atoms in solid materials (oxide such as $SiO_2$ and semiconductor such as Si and GaAs). This is a nature inherent to Pt and insertion of the barrier metal for improving the adhesion property is an essential method.

In view of the operation of the hydrogen sensor, there is a primary problem that a hydrogen gas is blocked or occluded in the barrier metal layer if the barrier metal layer is present and the sensor does not respond to hydrogen gas at all or the hydrogen response sensitivity is extremely lowered to inhibit the use as the sensor.

On the other hand, we also performed air annealing to a Pt (15 nm)/Ti (5 nm)/$SiO_2$ (18 nm)/Si stacked film MOS structure at 800° C. for 30 minutes to achieve a porous structure (for example, in Patent Literature 1, FIG. 18 shows a sensor principle explanatory view and FIG. 19 shows a cross sectional TEM image of gate). We have also performed air annealing to a Pt (15 nm)/Ti (5 nm)/SiO$_2$ (18 nm)/Si stacked MOS structure at 400° C. for 2 hours to achieve a hydrogen sensor using a Pt—Ti—O gate structure in which a Ti layer comprises a mixed layer of TiO$_x$ nanocrystals and an amorphous Ti doped with oxygen at an ultrahigh concentration, in which Ti and O are accumulated at high concentration in the Pt grain boundary to achieve extremely high sensitivity characteristics at 100 ppm to 1% hydrogen concentration diluted with air (for example, in Patent Literature 1, FIG. 12 shows a concentration dependency and high sensitive characteristics of sensor and FIG. 1 explain the gate structure thereof and FIG. 2 shows a cross sectional TEM image of the gate). This Pt—Ti—O gate structure has excellent characteristics having a life time of the intrinsic chip for 10 years or more as the characteristics thereof (for example, refer to Usagawa, et al. Fuel Cell, Vol 8, No. 3, 2009, pp. 88 to 96 (Non-Patent Literature 8)), and it was found that the reproducibility of the threshold voltage Vth and the uniformity in wafer were improved outstandingly by applying a hydrogen annealing treatment (for example, in Patent Literature 2, FIG. 7(*a*)). However, the Pt—Ti—O gate structure does not respond to 0.1 to 1.0% methane, 0.1% ethane, 0.1% CO, and 817 ppm isooctane at an operation temperature of 115° C. (Non-Patent Literature 8).

The problems of the barrier metal have been solved by using the Pt—Ti—O gate structure invented by the technique in the prior application (Patent Literature 1).

CITATION LIST

Patent Literature

Patent Literature 1: Japanese Patent Unexamined Application Publication No. 2009-300297
Patent Literature 2: Japanese Patent Unexamined Application Publication No. 2009-254522

Non-Patent Literature

Non-Patent Literature 1: Shimizu, et al. Applied Physics, Vol 70, No. 4 (2001), 423-427
Non-Patent Literature 2: I. Simon, et al., Sensor and Actuators B Vol. 73 (2001) pp. 1-26
Non-Patent Literature 3: T. Suzuki, et al. The 10th Int. Meeting, Chemical Sensors, 3B02, Jul. 11-14, 2004, Tsukuba, Japan
Non-Patent Literature 4: F, Winquist, et al. Appl. Phys. Vol, 43 (1983), pp. 839-841
Non-Patent Literature 5: K. Dobos, et al., IEEE ED vol. ED-32 (1985), pp. 1165-1169
Non-Patent Literature 6: H. Dannetun, et al., Appl. Phys. vol. 66 (1989), pp. 1397-1402
Non-patent Literature 7: I. Lundstrom, et al. Sensors and Actuators, B1 (1990) 15-20
Non-Patent Literature 8: Usagawa, et al. Fuel Cell, Vol. 8, No. 3 (2009) 86-96

SUMMARY OF THE INVENTION

Technical Problem

The existent Pt—Ti—O gate structures described above involve the following subjects.
(1) The Pt—Ti—O gate structure scarcely responds to those other than hydrogen and the selectivity is excessively strong compared with commercial hydrogen sensors (catalytic combustion type, metal-oxide semiconductor type, gas thermal conduction type, solid electrolyte type).
(2) The Pt—Ti—O gate structure based on the Pt (15 nm)/Ti (5 nm)/SiO$_2$ (18 nm)/Si stacked film MOS structure does not respond to hydrogen at a concentration in air of about 70 ppm or less. Further, at a concentration of about 10% or more, the sensor response intensity $\Delta V_g$ is saturated in a higher concentration region.
(3) In the porous structure achieved in air at 800° C. for 30 minutes (refer to Patent Literature 1), the gap between the Pt grains is excessively long to decrease the electric capacitance and, as a result, the sensitivity is low, control for the gap length is difficult, and the Pt film tends to be peeled since the gap between the Pt grains is formed of air.
(4) Further, in the porous structure (refer to Patent Literature 1), since treatment is performed at a high temperature, a high temperature heat treatment has to be applied before formation of the metal and the Pt grain gap portion is covered with an insulating film in the subsequent step. In the process of removing the insulating film of the gate region at the final stage of the processing steps, the Pt grains are excessively thin and the insulating film cannot be removed easily while skillfully leaving the gap and, as a result, controllability to the electric capacitance is worsened.

Then, the purposes of the present invention for solving the subject (1) to (4) are to be described below.

The purpose (first purpose) of the present invention is to provide a hyper thin film gas sensor capable of coping with sensing of hydrogen and various other gases, and having high reliability, particularly, high long-term reliability, as well as a method of manufacturing the same by applying a nano-scaled composite thin film having a feature of forming a metal compound (nano compound) in a nano space of hyper thin film platinum grain boundaries to the sensing film of a gas sensor and changing the constituent metal of platinum and the nano compound, the film thickness, the occupancy ratio, and forming condition.

Further, other purpose (second purpose) of the invention is to provide a hyper thin film gas sensor capable of achieving reading of the amount of charges accumulated in an electric capacitance by deposition of an adsorbed gas molecule in the electric capacitance between platinum grains and the nano metal compound of a hyper thin film as a voltage signal, as well as a manufacturing method thereof by provision of a nano-scaled composite thin film capable of controlling the occupancy ratio of the platinum grains and the nano metal compound of the hyper thin film.

Further, other purpose (third purpose) of the present invention is to provide a hyper thin film gas sensor capable of achieving reading for the change of electric resistance of the nano-scaled composite thin film by deposition of an adsorbed gas molecule to a nano metal compound as current change, voltage change or resistance change, as well as a method of manufacturing the same by provision of a nano-scaled composite thin film having further increased occupancy ratio of the nano metal compound compared with platinum grains of hyper thin film or having a nano metal compound in which conductive carriers are present.

Further, other purpose (fourth purpose) of the invention is to improve the reliability of a sensor chip per se mounted on a gas sensor. In the existent Pt porous gate structure, since the gap between the Pt grains is a space with no presence of solid substance (refer to as an air gap) and, further, Pt grains are formed directly on the insulating film, for example, of SiO$_2$, SiN, and Ta$_2$O$_5$ to form a easily peelable structure, it involves a problem that the adhesion property between the Pt and the gate insulating film is poor and no long-term reliability can be ensured. Now, the invention intends to provide a hyper thin film gas sensor of high long-term reliability and a method of manufacturing the same by forming the underlayer film of the nano-scaled composite thin film with a thin film containing the metal compound forming the nano-scaled thin film.

Further, other purpose (fifth purpose) of the invention is to provide a hydrogen sensor operating at several hundred ppm or less and down to about several ppm, and a hydrogen sensor operating in a concentration region of several % more and up to about several tens %.

Further, other purpose (sixth purpose) of the invention is to provide a gas sensor in which the nano-scaled composite thin film and the underlayer film described above are formed on a semiconductor substrate such as silicon, SiC, GaN, or GaAs, as well as a method of manufacturing the same.

Further, other purpose (seventh purpose) of the invention is to provide a heat insulating structure in which an MEMS structure is applied to the sensor structure for achieving the purposes described above, thereby being capable of reducing the consumption power to about 1/100 or less and lowering the temperature of the sensor substrate for the portion other than the sensor portion to 125° C. or lower compared with those before application of the structure.

Solution to Problem

Among the inventions disclosed in the present application, the outline of typical inventions are to be described simply as below.

A gas sensor according to a typical embodiment includes (a) a gate insulating film disposed over a substrate and (b) a gate electrode disposed over the gate insulating film in which electric changes caused by a gas molecule to be detected adsorbed on the gate electrode are detected by way of the gate insulating film, in which the gate electrode has (b1) a metal oxide mixed film where an oxygen doped amorphous metal containing oxygen and the metal oxide crystals are mixed and (b2) a platinum film disposed over the metal oxide mixed film, the platinum film comprises a plurality of platinum crystal grains and a grain boundary region present between the platinum crystal grains, and the grain boundary region is filled with the metal oxide mixture, and the periphery of the platinum crystal grains is surrounded by the metal oxide mixture.

Further, a gas sensor according to a typical embodiment includes (a) lower electrode comprising a semiconductor substrate, (b) a capacitive insulating film formed over the lower electrode, and (c) an upper electrode formed over the capacitive insulation film in which electric changes caused by a gas molecule to be detected adsorbed on the gate electrode are detected by way of the gate insulating film in which the upper electrode has (c1) a metal oxide mixed film where an oxygen-doped amorphous metal containing oxygen and metal oxide crystals are mixed, and (c2) a platinum film disposed over the metal oxide mixed layer, the platinum film comprises a plurality of platinum crystal grains and a grain boundary region present between each of the platinum crystal grains, and the grain boundary region is filled with the metal oxide mixture, and the periphery of the platinum crystal grain is surrounded by the metal oxide mixture.

Further, a gas sensor according to a typical embodiment includes a gas sensor including a sensor chip where an MOS structure gas sensor and a heater are formed on the main surface of a substrate, a mounting substrate for mounting the sensor chip, and a heat insulating material interposed between the sensor chip and the mounting substrate in which the sensor chip has an MEMS region formed by boring the rear side of the substrate, a heater region having the heater formed therein and formed on the side of the surface of a substrate over the MEMS region, and pad electrodes formed on the surface of the substrate and connected by way of the lead wiring to the heater, and the mounting substrate has lead terminals penetrating the mounting substrate and used for connection with the outside, and lead wirings for connecting the pad electrodes and the lead terminals in which, a thermal resistance $R_P$ from the heater region through the edge of the MEMS region to the mounting substrate is represented as: $R_P = R_M + R_S \cdot R_L/(R_S + R_L)$, where $R_D$ represents a thermal resistance from the heater region through a bored cavity in the MEMS region to the mounting substrate that sandwiches the heat insulating material relative to the sensor chip, $R_M$ represents a thermal resistance from the heater region to the edge of the MEMS region, $R_S$ represents a thermal resistance from the edge of the MEMS region through the silicon substrate and from the heat insulating material to the mounting substrate, and $R_L$ represents a thermal resistance for the sum of a thermal resistance from the edge of the MEMS region to the pad electrode and a thermal resistance of the lead wire, and the thermal resistances $R_D$, $R_P$ and the surface area of the heater region are defined so as to satisfy: $\text{Powmax}/\Delta T\max > 1/R_D + 1/R_P + 4\pi\lambda \cdot r_A$ where $r_A$ represents a radius of a circle having an area identical with the surface area of the heater region, $\lambda$ represents a thermal conductivity of an atmospheric gas due to the heating of the heater, $\Delta T\max$ represents a difference between a set temperature of the heater region and an assumed environmental lowest temperature for installation, and Powmax represents a heater maximum power charged to the heater which is determined by an electric resistance of the heater and a power source voltage at the set temperature, when the heater maximum power is 25 mW or less.

Further, a method of manufacturing a gas sensor according to a typical embodiment includes,
(a) a step of forming a gate insulating film over a semiconductor substrate, and
(b) a step of forming, after the step (a), a gate electrode over the gate insulating film in which Ti at a thickness of 3 to 6 nm is deposited over the gate insulating film and, subsequently, Pt is deposited over Ti at a ratio of Pt and Ti within a range of about 1:1 to 1:5 in the step of forming the gate electrode, and heating is performed in an oxygen atmospheric gas diluted with nitrogen or argon at a temperature within a range from 400° C. to 650° C. for about 20 minutes to 2 hours.

Advantageous Effects of Invention

The effects obtained by typical invention among those disclosed in the present application are to be described simply as below.

A hyper thin film gas sensor capable of coping with sensing of hydrogen and various other gases and having reliability, particularly, high long-term reliability, as well as a method of manufacturing the same are obtained by applying a nano-scaled composite thin film having a feature of forming a metal compound (nano compound) in grain boundary nano space of a hyper thin platinum film and changing the constituent metals of platinum and the nano compound, film thickness, occupancy ratio, and the forming conditions.

DESCRIPTION OF EMBODIMENTS

Figure 1A:
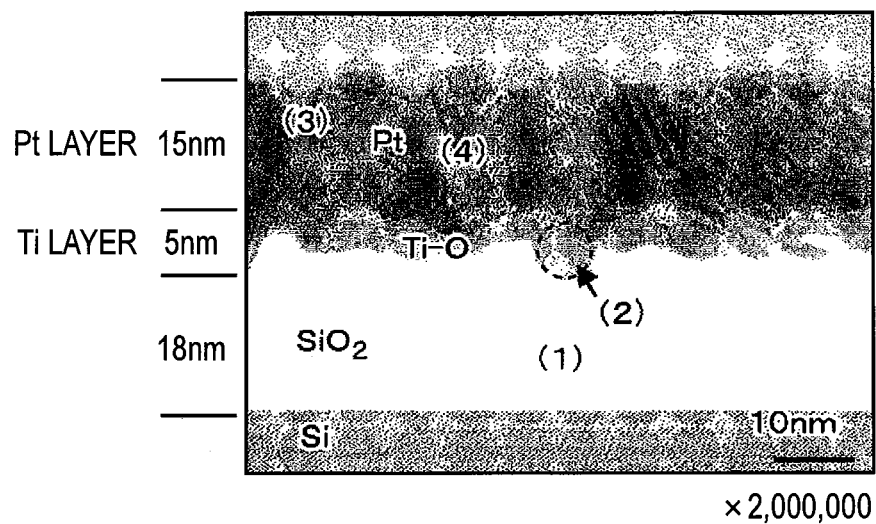
FIG. 1A is a cross sectional TEM (transmission electron microscope) photograph showing a gate electrode and a stacked structure just therebelow in a Pt—Ti—O gate Si-MOSFET hydrogen gas sensor using a platinum film as a gate electrode.

In the following embodiments, description is to be made while dividing into a plurality of sections or embodiments when this is necessary for the sake of convenience. However, they are not irrelevant to each other unless otherwise specified but are in such a relation that one is modifications, details, supplementary explanation, etc. of a part or entirety of other.

Further, in the following embodiments, when numbers of elements, etc. (including number of pieces, numerical values, quantity, range, etc.) are referred to, they are not restricted to the specified number but may be more than or less than the specified number unless otherwise specified or they are apparently restricted to the specified numbers in principle.

Further, in the following embodiments, it is needless to say that the components (also including elements steps, etc.) are not always indispensable unless otherwise specified or apparently considered as indispensable in principle.

In the same manner, when the shape, positional relation, etc. of the components, etc. are referred to in the following embodiments, they include those which are substantially approximate to or similar with the shape, etc. unless otherwise specified and considered apparently not in principle. This is applicable also to the numerical values and the ranges described above.

Further, throughout the drawings for explaining the following embodiments, identical components carry the same references as a rule, for which duplicate descriptions are to be omitted. Further even plan views may be sometimes hatched in order to make the drawing easy to see.

First Embodiment

At first, the techniques investigated by the present inventors are to be described. FIG. 1A illustrates a TEM (transmission electron microscopy) observation image for a gate electrode portion of a Pt—Ti—O gate structure shown in the Patent Literature 1 described above, and FIG. 1B shows a schematic view thereof. A sample in FIG. 1A used for observation is prepared by forming a Pt (15 nm)/Ti (5 nm)/SiO$_2$ (18 nm)/Si stacked film MOS structure by an electron beam vapor deposition method (EB vapor deposition), subsequently, applying semiconductor processing steps, then removing a protective insulating film over a gate electrode, and then subjecting them to an annealing treatment in air at 1 atm, at 400° C., for 2 hours.

As a feature of the structure, agglomerates 77a of Ti and O are formed in a Pt grain boundary region 77 (shown by (3) and (4) in FIG. 1A), the Pt grain boundary region is effectively extended, and a hydrogen permeating corridor 77a is formed. Assuming the agglomerates of Ti and O present in the corridor as a TiO$_x$ nanostructure, the Pt layer can be regarded as a nano-scaled composite structure of Pt and TiO$_x$ nanostructure where TiO$_x$ nanostructures are arranged at the periphery of the Pt grains.

In the upper portion of the grain boundary region in the schematic view 1B, small crystals 2c comprising an oxygen-doped titanium or titanium oxide are formed. Further, a Ti layer 2 therebelow is formed of a mixed film (mixed metal oxide film) of TiO$_x$ nano crystal 2a (metal oxide crystals shown by (2) in FIG. 1A) and amorphous Ti doped with oxygen at an extremely high concentration (oxygen-doped amorphous metal) 2b. It is considered that Ti and oxygen serve as an adhesive of bonding the Pt grains to each other in the mixed layer and the problem of long-term reliability such as occurrence of film peeling or cracking can be overcome.

On the other hand, we also performed annealing in air at 800° C. for 30 minutes to a Pt (15 nm)/Ti (5 nm)/SiO$_2$ (18 nm)/Si stacked film MOS structure to achieve a porous structure (for example, in Japanese Unexamined Patent Application Publication No. 2009-300297 (Patent Literature 1)). FIG. 1C shows a cross sectional TEM photograph when an annealing treatment is applied to the Pt/Ti/SiO$_2$/Si structure in air at a heat treatment temperature of 800° C. for a heat treatment time of 30 minutes (refer to FIG. 1C(a)), and a Pt/Ti/SiO$_2$/Si structure before the annealing treatment in the region on the right of FIG. 1C(a) (refer to FIG. 1C(b)). It can be seen, from the cross sectional TEM photograph shown in FIG. 1C(a), that the thickness of the titanium film and the thickness of the platinum film change greatly after the annealing treatment. It has been known in this case that the titanium film substantially comprises crystals 88 of TiO$_2$ (rutile structure) in view of X-ray diffraction of the titanium film. It can be seen that also the morphology of the platinum film is greatly different from the gate structure after the annealing treatment at a heat treatment temperature of 400° C. for a heat treatment time of 2 hours shown in FIG. 1A.

Figure 1B:
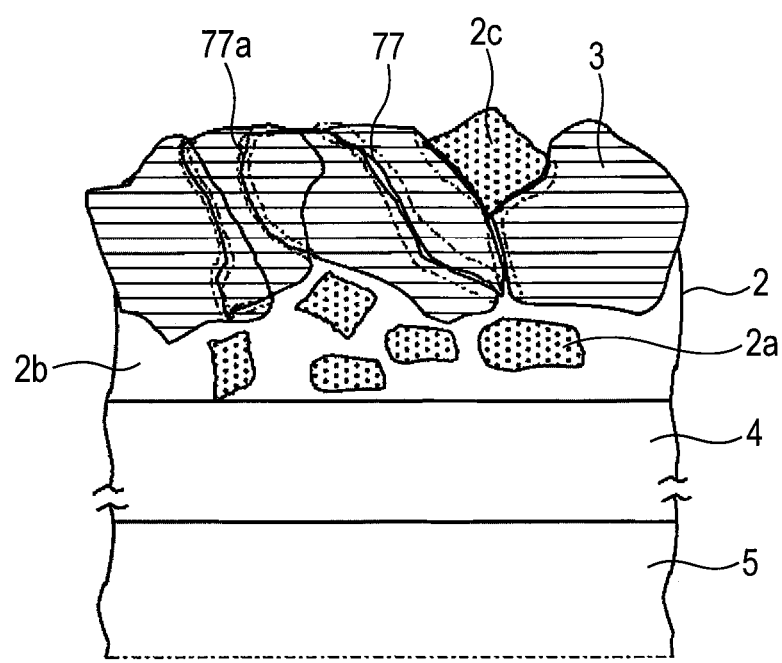
FIG. 1B is a schematic view showing a gate electrode and a stacked structure just therebelow in an Si-MOSFET hydrogen gas sensor (FIG. 1A) using a platinum film as a gate electrode.
Figure 1C:
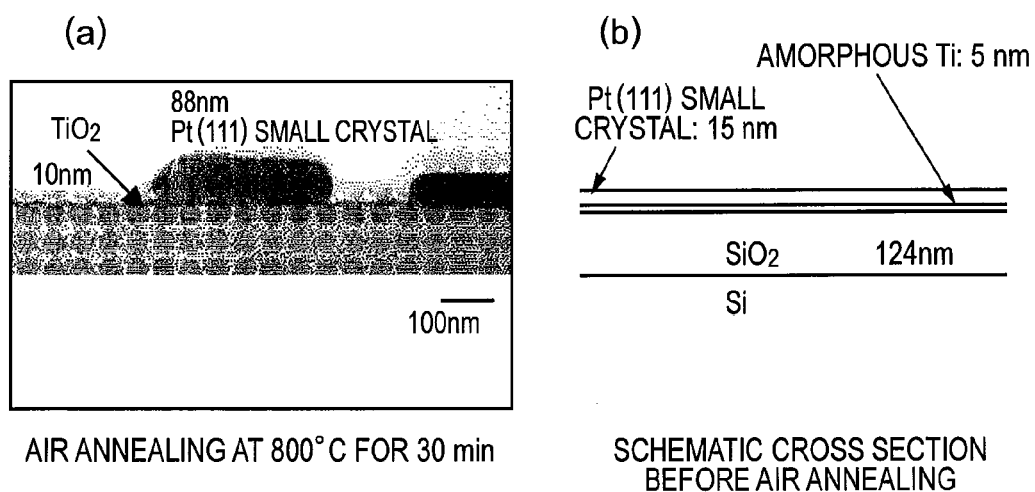
FIG. 1C (a) is a cross sectional TEM photograph when a Pt/Ti/SiO$_2$/Si structure is put to an annealing treatment in air at a heat treatment temperature of 800° C. for a heat treatment time of 30 min and (b) is a schematic view showing a Pt/Ti/SiO$_2$/Si structure before the annealing treatment.
Figure 1D:
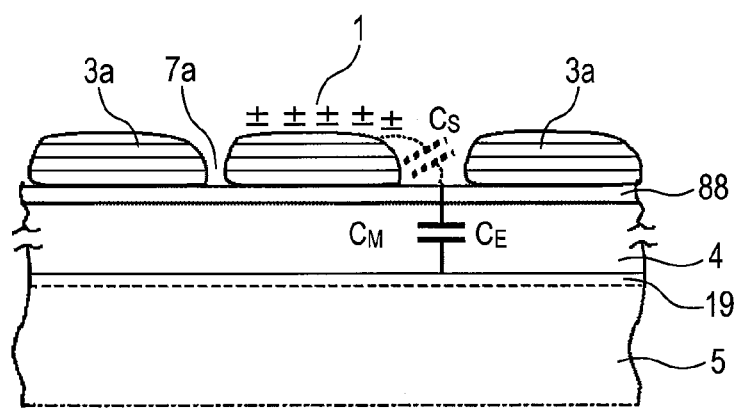
FIG. 1D is a view schematically showing a porous gate structure in an Si-MOSFET gas sensor using platinum as a gate electrode.

Successively, the operation principle of a gas sensor in this structure is to be described while referring to a cross sectional TEM photographic view 1C(a) and FIG. 1D as a schematic view thereof. FIG. 1D is a view schematically showing a gate structure. In FIG. 1D, a gate insulating film 4 comprising silicon oxide is formed over a semiconductor substrate 5 comprising silicon. Then, a titanium oxide film 88 is formed over the gate insulating film 4. The titanium oxide film is a thin film comprising titanium oxide small crystals having a rutile structure, a thin film comprising titanium oxide small crystals in which an anatase structure is mixed in addition to the rutile structure, or a thin film of titanium oxide small crystals mixed with an oxygen-doped titanium film.

Referring to the mechanism of sensor response, as discussed in Sensors and Actuators, B1 (1990) 15-20 (Non-Patent Literature 7) and reference documents therein, an ammonia gas, a CO gas, a methane gas or the like is deposited on the surface of an island shape platinum small crystal 3a to cause an effective molecule polarization 1 by electric dipole moment due to the asymmetricity of a molecule per se or polarization of a molecule by adsorption also for a highly symmetric molecule thereby changing the surface potential φs of platinum small crystals 3a. Thus, in a capacitance system of an electric capacitance $C_S$ between a platinum small crystal 3a and a gap region (gap 7a) where platinum is not present on the surface of a gate insulating film 4, an electric capacitance $C_E$ between the gap region and the channel region 19, and an electric capacitance $C_M$ between the platinum small crystal 3a and the channel region 19, the electric capacitance $C_S$ and the electric capacitance $C_E$ are connected in series and the electric capacitance $C_M$ is connected in parallel. Accordingly, the surface potential φs and the amount of change Δφs are in a relation:

$$\Delta V = \Delta\phi s \cdot C_S \cdot C_E / [C_S \cdot C_E + C_M(C_S + C_E)] \quad \text{formula (1)},$$

and change ΔV of the gate potential relative to the gas adsorption can be measured. As described above, the gas sensor in the first embodiment can detect a gas concentration as the change ΔV of the gate potential. That is, this means that the gas sensor in the first embodiment can detect a gas so long as the gas changes the surface potential of the platinum small crystal in view of the operation principle described above. Further, while an insulation material is sometimes formed in the gap 7a shown in FIG. 1D in the manufacturing step, the gas concentration can be detected also in such a case by the operation described above as the gas sensor. The gate structure of the gas sensor has a feature that the grain boundary region between platinum small crystals 3a oriented in the (111) direction is eliminated to form a gap 7a between the platinum small crystals 21a.

Figure 1E:
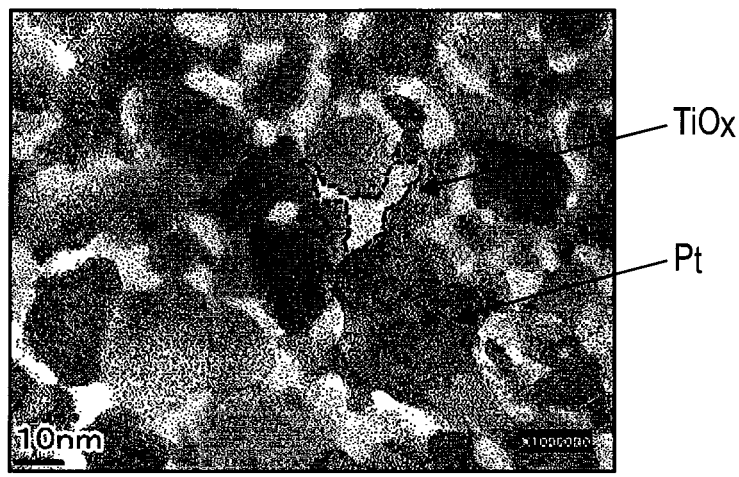
FIG. 1E is a planar TEM (transmission electron microscopy) photograph as viewed from the upper surface of the gate electrode in a Pt/Ti/O-gate Si-MOSFET hydrogen gas sensor using the platinum film as a gate electrode.
Figure 1F:
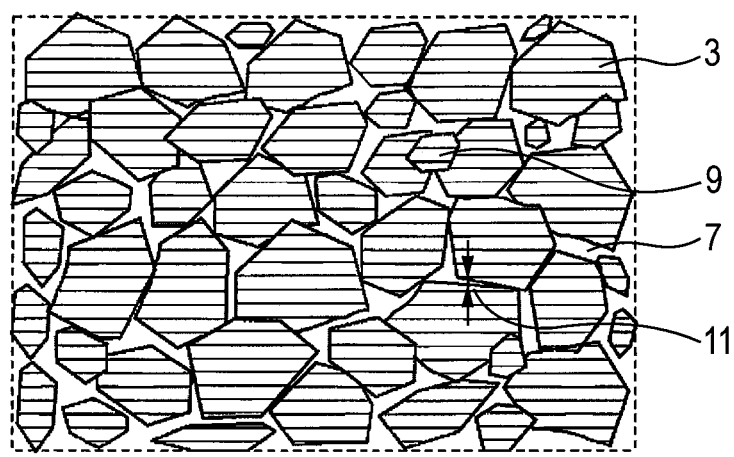
FIG. 1F is a schematic view as viewed from an upper surface of the gate electrode in the Pt/Ti/O-gate Si-MOSFET hydrogen gas sensor using the platinum film as a gate electrode.

Then, with a purpose of closely examining the Pt—Ti—O gate structure shown in FIG. 1A and FIG. 1B, the gate electrode in FIG. 1A was put to planar TEM observation from the direction of the surface of the gate electrode in FIG. 1A to obtain an observation image shown in FIG. 1E. As a result, it has been found in view of FIG. 1E that a nano-scaled structure of Pt crystal grains of 5 to 20 nm and titanium oxide TiO$_x$ of several nm (dotted region: although amorphous titanium doped with oxygen at a ultrahigh concentration is mixed, this is referred to hereinafter as TiO$_x$). Based on the result of X-ray analysis, it has been known that the platinum grains form a thin film in which small crystals of a fcc (face-centered cubic lattice) crystal structure are oriented in the (111) direction. In view of the planar TEM observation, a schematic view of FIG. 1F was obtained as a Pt—Ti—O gate structure. This is a structure in which titanium oxide TiO$_x$ 7 is coarsely scattered at the platinum grain boundary while platinum grains 3 are in contact to each other. The platinum grain 3 and the platinum grain 3 are distributed with gaps as shown in the drawing, and the average gap 11 is small. In the Pt—Ti—O gate structure shown in FIG. 1F, the occupational portion of TiO$_x$ nanostructure present between the Pt grain boundaries is small in the nanostructure, and Pt grains are in contact to each other and electrically short circuited in most of the portions. In this case, regions 9 where platinum grains are in contact and overlap each other are present at a considerably high probability.

On the other hand, in the porous structure shown in FIG. 1C(a) and FIG. 1D, since the width of the gap 7a formed between the platinum small crystals is as large as about 100 nm and the capacitance Cs is too small to lower the sensitivity and the gap 7a is a vacant gap, which result in significant problems as the device structure. With a practical point of view, the width of the gap 7a formed between the platinum small crystals is preferably about from several nm to 10 nm. However, since gate structures of different forms (FIG. 1A, FIG. 1B and FIG. 1C and FIG. 1D) are achieved starting from the Pt/Ti/SiO$_2$/Si structure of an identical film thickness, a new device to be shown later can be created by investigation of the film thickness and, the thickness ratio, the film thickness structure of Pt and Ti, investigation of metals other than Ti and, further, investigation and change of annealing conditions.

When the TiO$_x$ nanostructure occupies the gap between the Pt grain boundaries, that is, a structure where the Pt grain is surrounded with the TiO$_x$ nanostructure by intentionally controlling the statistic ratio (area ratio or volume ratio) between both of the TiO$_x$ nanostructure and the Pt grains formed in the nano space of the ultra-thin film Pt grain boundary, a structure where the Pt grains are connected to each other by capacitive coupling is achieved. Thus, the porous Pt gate structure explained in the section of the prior art can be achieved effectively and the vacant space between the Pt grains does not remain vacant but can be filled with the TiO$_x$ nanostructure. The structure has an extremely high dielectric constant compared with vacuum and the electric capacitance is effectively increased by so much as the dielectric constant thereof when compared for an identical capacitance size and the sensitivity is increased effectively by so much as the dielectric constant.

In the case of the vacant space, it is necessary to fill the space with an insulating film, for example, of SiO$_2$, PSG (phosphorus doped glass) or silicon nitride (SiN) and finally remove the insulating film in the sensor gate portion after forming the gate and a technique of removing the film while leaving only the portion of the vacant space is necessary. However, when the space is filled with the TiO$_x$ nanostructure, it is easy to selectively remove the insulating film just over the TiO$_x$ nanostructure. Further, as the most prominent feature, an effect of remarkably increasing the adhesion property on the gate insulating film is provided by adopting the nano-scaled structure for the TiO$_x$ nanostructure and adopting a specific form of the Ti mixed layer. That is, a high reliability can be achieved in view of the form of the Pt—Ti—O structure compared with the porous Pt gate structure investigated so far.

A schematic cross sectional view of a gate (FIG. 2A) and a schematic view of a planar gate electrode (FIG. 2B) show a case of applying "second object" of the present invention described previously to the gate electrode of an Si-MOS (metal-Oxide-Semiconductor) structure. The schematic cross sectional view of the gate (FIG. 2A) shows a structure comprising a silicon substrate 5, a gate insulating film SiO$_2$ 4 formed thereover, a mixed film of TiO$_x$ nano crystals 2a and an amorphous Ti 2a doped with oxygen at an extremely high concentration (referred to herein as a Ti mixed layer 2) formed thereover, and (111)-oriented Pt grains 3 effectively formed thereover and surrounded with TiO$_x$ nanostructures 7. In the drawing, an inversion layer 19 is formed. The planar view (FIG. 2B) shows a structure in which the (111)-oriented Pt grains 3 are effectively surrounded with the TiO$_x$ nanostructures 7. The structure has a feature that the average gap 11 between the Pt grains 3 to each other is wide and the Pt grains are connected by means of a capacitive coupling and the structure less includes portions 9 where Pt grains are electrically short-circuited to each other, different from the Pt—Ti—O gate structure shown in FIG. 1F. Thus, the molecule adsorption amount can be sensed as the variation amount ΔV of a threshold voltage Vth (or flat band voltage VF) of an MOS structure as the potential change due to the change of the surface potential φs by an adsorption gas shown by the formula (1). Actually, for increasing the electric capacitance, the average inter Pt grain distance 11 is preferably about 1 nm to 10 nm. This structure also has other features that the dielectric constant is high as in the TiO$_x$ nanostructure 7 and carriers are scarcely present in the TiO$_x$ nanostructure. In this case, free carriers such as electrons and holes are not present effectively or present only slightly in the TiO$_x$ nanostructure 7. The average inter-Pt grain distance 11 is made small in order to increase the electric capacitance and even if in a case of a conductive oxide where carriers are present in a bulk state at a concentration, for example, of $10^{21}$ N/cm$^3$ or more (upper limit is a solid solution limit (TiO$_2$)), the inside of the TiO$_x$ nanostructure 7 is completely depleted due to the Schottky barrier between the Pt grain 3 and the TiO$_x$ nanostructure 7 as the feature of this structure if the gap is (narrowed to) about several nm. The feature in view of the structure is that it less includes portions 9 where Pt grains are electrically short-circuited to each other. However, the TiO$_x$ nanostructure 7 is an insulator in a completely depleted state or in which carriers are not present at the operation temperature.

A schematic cross sectional view of a gate (FIG. 2C) and a schematic planar view of a gate electrode (FIG. 2D) show a case of applying "third object" of the invention described above to the gate electrode of an Si-MOS (Metal-Oxide-Semiconductor) structure. Descriptions to be made to a case of using Sn (tin) instead of Ti. The schematic cross sectional view of the gate (FIG. 2C) shows a structure comprising a silicon substrate 5a, a gate insulating film SiO$_2$ 4 formed thereover, a mixed film of SiO$_x$ nano crystals 2a and an amorphous Sn 2b doped with oxygen at an extremely high concentration (referred to herein as Sn mixed layer) formed thereover and (Pt grains 3 effectively formed thereover and surrounded by the SnO$_x$ nanostructure 7. The planar view (FIG. 2D) shows the structure in which the Pt grains 3 are effectively surrounded with the SnO$_x$ nanostructure 7. The structure has a feature that the average distance 11 between each of the Pt grains is as large as several nm or more, or the SiO$_x$ nanostructure 7 has semiconductor characteristics and conductive carriers are present, different from the structure shown in FIG. 2A and FIG. 2B. The electron concentration can be changed about from $10^{15}$ N/cm$^3$ to $2\times10^{20}$ N/cm$^3$ depending on the extent of oxidation (compositional ratio x) in the case of tin oxide SnO$_x$ which is substantially an n-type semiconductor.

When the structure is exposed to atmospheric air, since the SnO$_x$ nanostructure 7 is formed so as to surround the platinum grain 3, and the platinum grain 3 and the SnO$_x$ nanostructure 7 are in contact with each other, so-called depletion layers 6, 6a are formed in the nanostructure 7 from the boundary thereof in the Sn nanostructure 7. When a reducing gas such as an ammonia gas, a CO gas, or a methane gas is deposited to the surface of the SnO$_x$ nanostructure 7, effective polarization 1 is generated to a molecule by electric dipole moment due to asymmetricity of the molecule per se or polarization of a molecule by adsorption even if a molecule is highly symmetric to change the surface potential φs of the SnO$_x$ nanostructure 7, and depletion layers 6, 6a in the SiO$_x$ nanostructure 7 shrink as depletion layers 10, 10a. When an oxidizing gas is deposited, the thickness of the depletion layers 6, 6a in the $SiO_x$ nanostructure 7 extend on the contrary (not illustrated in the drawing). This structure relies on the change of the electric resistance in the in-plane direction of the gate electrode depending on the presence or absence of gas adsorption as the principle of sensing, and does not utilize the MOSFET operation. However, since the gate structure is formed by forming an insulating film over the Si substrate, this is referred to as a gate electrode for the sake of convenience (not controlling carriers) assuming this as a MOS structure in a broad sense in view of the structure.

While description has been made to a case of Pt and $TiO_x$ or SnO, the invention is applicable also to any other material than Pt that is less oxidizable and has a catalytic effect since the structure found by us has a feature that the structure can be realized by skillfully utilizing the property of the platinum film that is less oxidizable at a high temperature. Such material includes, for example, Ir (iridium), Ru (ruthenium), La (lanthanum) and, further, alloys of the metals with Pt, or alloys of metals to each other. Considering mainly for the catalytic function of Pt, it is not necessary that the underlying metal is a Ti layer and also the annealing treatment is not necessarily applied in air. Particularly, metals applicable in the form of metal oxides to gas sensors can be used. In addition to Ti, they includes, for example, tin (Sn), indium (In), iron (Fe), cobalt (Co), tungsten (W), molybdenum (Mo) film, tantalum (Ta) film, niobium (Nb) film, chromium (Cr), and Nickel (Ni).

If it is possible to develop a technique of intentionally controlling the statistic ratio between the Pt grain size and the metal compound nano-scale composite region (area ratio and volume ratio) by a film formation method (EB vapor deposition, sputtering method), control for each of the film thickness and the thickness ratio, and control for the annealing conditions in air or other gases in the ultra-thin film of two layer structure of metals such as Pt/Ti, and design the occupational ratio of the metal compound formed in the nano space of the Pt grain boundary, a group of various kinds of gas sensors can be constructed over an Si substrate (silicon platform), which was impossible so far.

Figure 3:
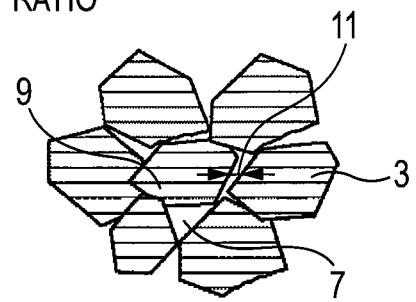
FIG. 3 (a), (b), (c) are views explaining the difference of functions of the nano-scaled structures described above respectively.
Figure 3:
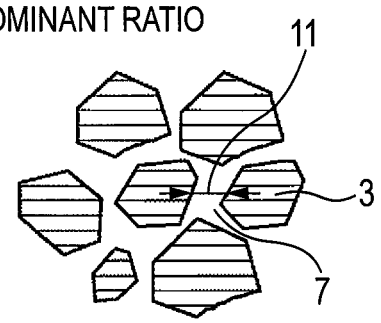
Figure 3:
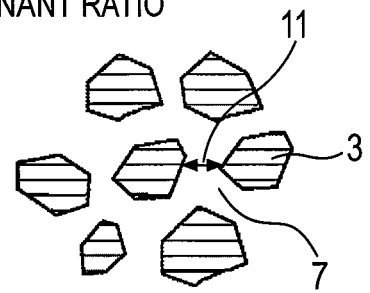

The principle of the gas sensor according to the invention can be shown as in FIG. 3 by summarizing the Pt/Ti system explained so far. FIG. 3 shows a material structure (nano-scaled structure) when the gate electrode is observed in a plane view.

FIG. 3(a) is a planar view of a gate electrode in the Pt—Ti—O gate structure of the existent inventions. The Pt—Ti—O gate structure includes less occupational portions of a $TiO_x$ nanostructure 7 present between the Pt grain boundaries, in which Pt grains 3 are in contact to each other and Pt grains 3 electrically short-circuit to each other in most of places. In this case, regions 9 where the platinum grains are in contact and overlap to each other are present at a considerably high probability. This is referred to as a Pt-dominant form. The Pt-grain boundary region is extremely narrow and has a selective sensitivity to hydrogen molecules.

Figure 2A:
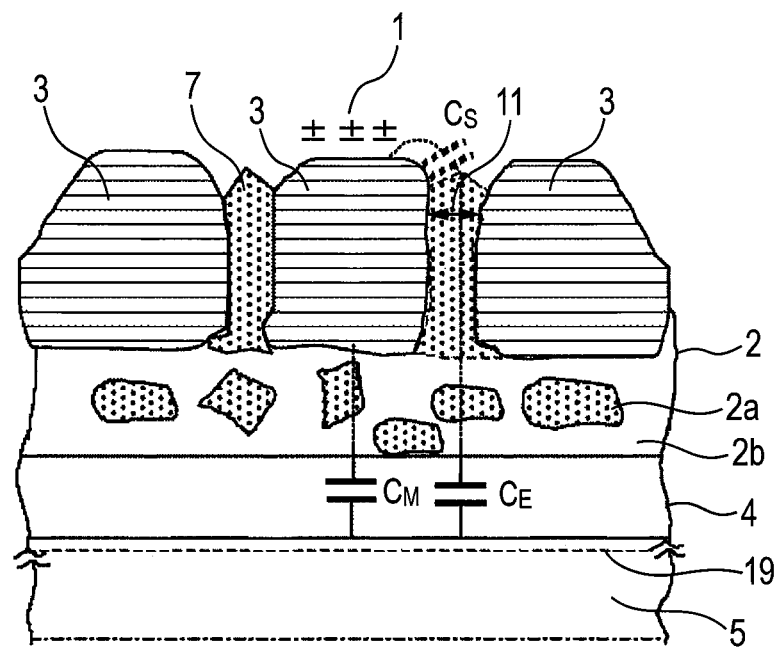
FIG. 2A is a cross sectional schematic view of a gate structure of an Si MOSFET gas sensor having a nano-scaled structure comprising platinum grains and TiO$_x$ nanostructure and having a capacitance-dominant structure of the present invention.
Figure 2B:
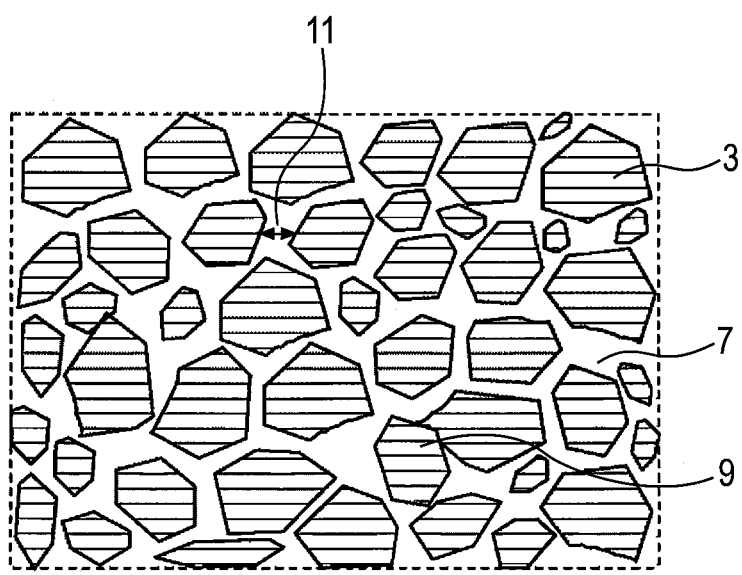
FIG. 2B is a schematic planar view of a gate structure of an Si MOSFET gas sensor having a nano-scaled structure comprising platinum grains and a TiO$_x$ nanostructure and having a capacitance-dominant structure as a gate electrode of the present invention.

FIG. 3(b) corresponds to FIG. 2B and shows a structure in which an average gap 11 between the Pt grains 3 to each other is wide and the Pt grains are connected by capacitive coupling and the structure scarcely includes or only slightly includes portions 9 where Pt grains electrically short-circuit to each other. However, The $TiO_x$ nanostructure 7 is an insulator in a completely depleted state or in which carriers are not present at a sensor operation temperature. This is referred to as a capacitance-dominant form.

Figure 2C:
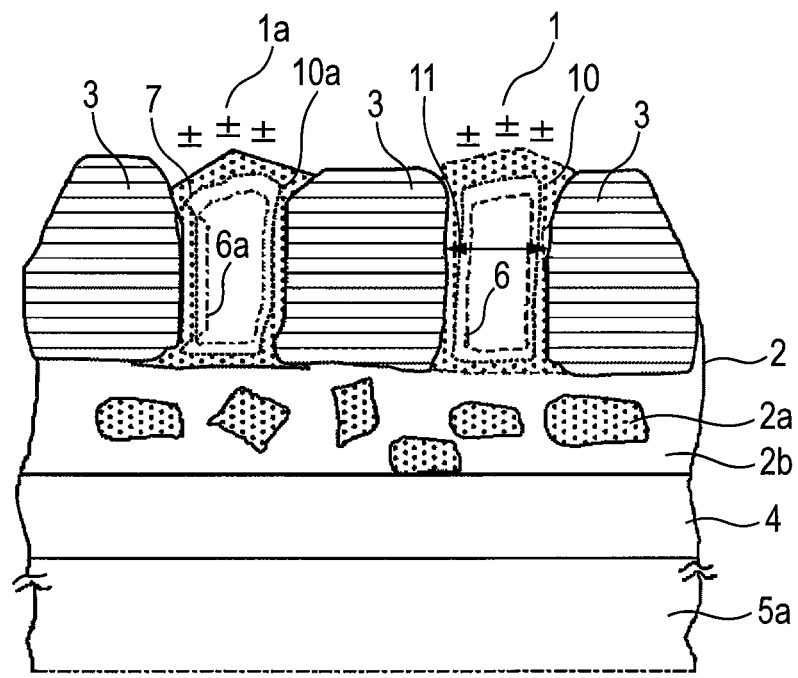
FIG. 2C is a schematic cross sectional view of a gate structure of an Si MOSFET gas sensor having a nano-scaled structure comprising platinum grains and an SnO$_x$ nanostructure and having a resistance-dominant structure as a gate electrode of the present invention.
Figure 2D:
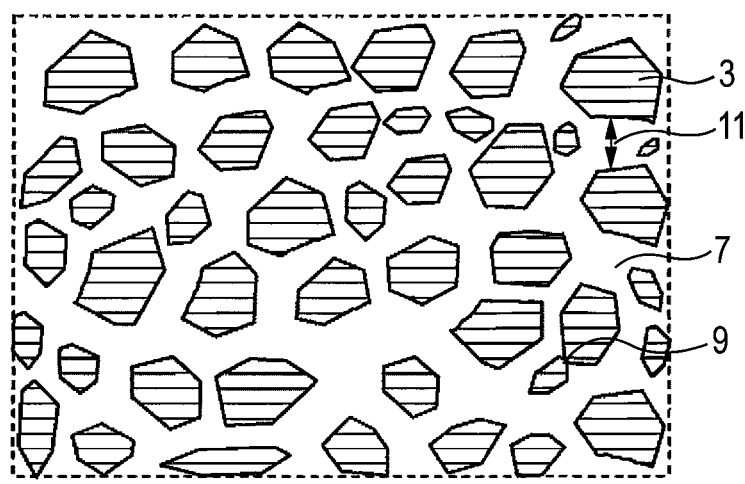
FIG. 2D is a schematic planar view of a gate structure of an Si MOSFET gas sensor having a nano-scaled structure comprising platinum grains and an SnO$_x$ nanostructure and having a resistance-dominant structure as a gate electrode of the present invention.

FIG. 3(c) corresponds to FIG. 2D and shows a structure in which an average gap 11 between Pt grains 3 is wider compared with that in FIG. 3(b), or Pt grains in a state where conductive carriers are present in the $TiO_x$ nanostructure 7 are connected by resistance coupling. This is a state in which the in-plane electric resistance of the structure is mainly determined depending on the resistance of the conductive carriers in the $TiO_x$ nanostructure 7 and the contact resistance between the Pt grain 3 and the $TiO_x$ nanostructure 7. The structure scarcely includes or only slightly includes portions 9 where Pt grains electrically short-circuit to each other. This is referred to as a resistance-dominant form.

Figure 4:
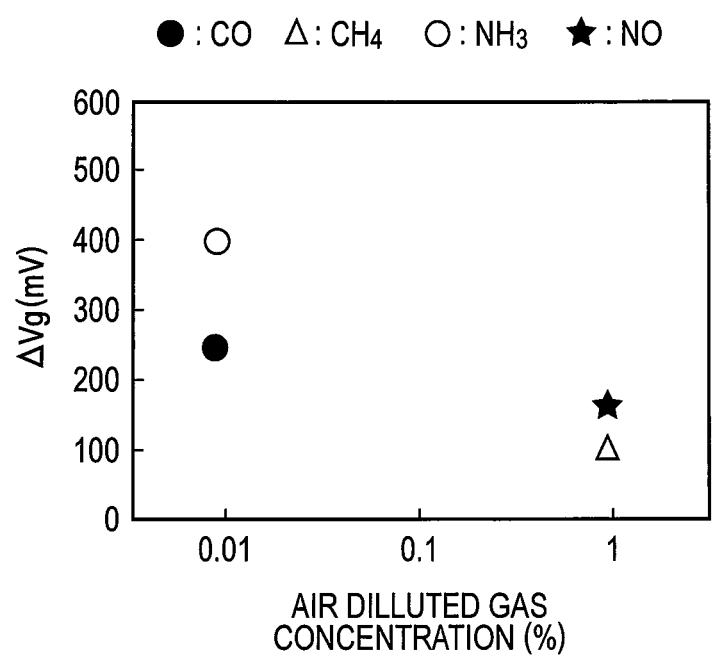
FIG. 4 is a view showing response characteristics of an Si-MOSFET gas sensor in which a gate electrode has a nano-scaled composite structure comprising platinum grains and a TiO$_x$ nanostructure and having a capacitance-dominant structure of the present invention to various kinds of gases.

A specific method of preparing the gate structure is to be described later. FIG. 4 shows data for an example corresponding to FIG. 2A and FIG. 2B when the invention is applied to the gate electrode of the Si MOSFET and the sensor response intensity $\Delta Vg$ to CO, $CH_4$, $NH_3$, and NO gas to the gas concentration in air. The operation temperature of the FET sensor is 150° C. For CO, $CH_4$, $NH_3$, and NO gases to which simple Pt—Ti—O structure did not respond so far, a response was obtained and, since the sensitivity is as high as several times or more compared with the existent porous structure, this shows that the present structure can be explained by the sensor principle formula (1). It is considered that the structure provides an effect by forming a plurality of nano capacitors in which a $TiO_x$ nanostructure of particularly high dielectric constant is inserted. For the response intensity $\Delta Vg$, a gate voltage Vg providing a source drain voltage Vds=1.5 V and a source drain current Ids=10 µA is defined as a threshold voltage Vth, which is defined as an absolute value for the Vth variation amount under gas radiation.

Figure 5A:
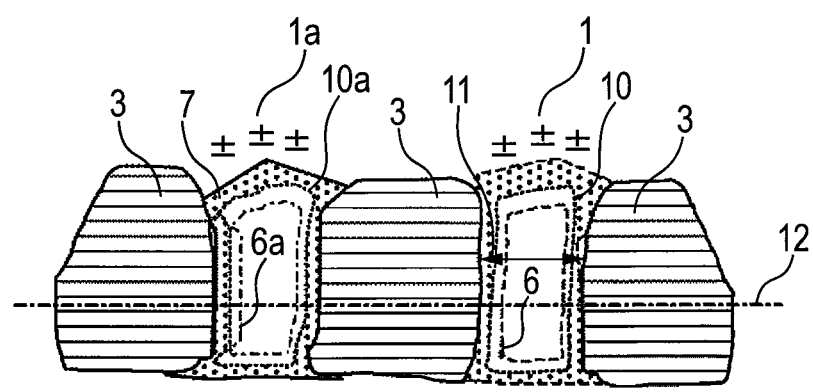
FIG. 5A is an explanatory view for an Si-MOS gate structure in which a gate electrode has a nano-scaled structure comprising platinum grains and an SnO$_x$ nanostructure and having a resistance-dominant structure of the present invention.
Figure 5B:
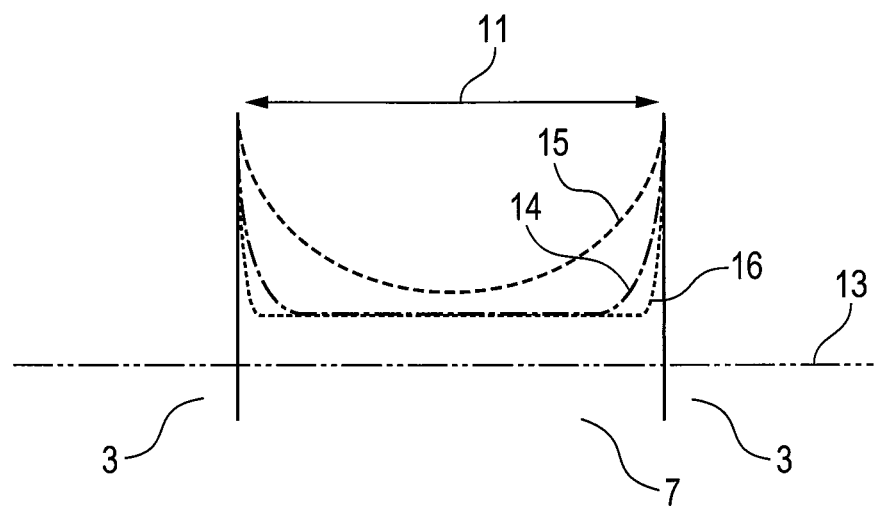
FIG. 5B is an energy band diagram of a gate electrode having a nano-scaled composite structure comprising platinum grains and an SnO$_x$ nanostructure and having a resistance-dominant structure of the present invention.

For the resistance-dominant form, a schematic view 2C for the cross sectional structure of a gate electrode portion is to be described more specifically. FIG. 5A shows a cross sectional structure for the Pt region in FIG. 2C. FIG. 5B shows an energy band diagram of Pt grains 3, an $SiO_x$ nanostructure 7, and Pt grain 3 at the line 12 shown in the diagram. In the drawing, reference 13 shows a Fermi level and the drawing shows a depletion layer 14 where the energy band of a conductor in the $SnO_x$ nanostructure 7 is in contact with the Pt grain 3 and extends from the junction barrier at the boundary thereof to the inside of the $SnO_x$ nanostructure 7. This is an energy band diagram upon exposed to air. A reducing gas, for example, an ammonia gas, a CO gas, or a methane gas is deposited at the surface of the $SnO_x$ nanostructure 7 in which effective polarization 1 is generated by an electric dipole moment due to the asymmetricity of a molecule per se or by polarization of a molecule by adsorption even if a molecule is highly symmetric to change the surface potential φs of the $SnO_x$ nanostructure 7, and the depletion layer 14 in the $SnO_x$ nanostructure 7 shrinks like a depletion layer 16. When an oxidizing gas such as an $NO_2$ gas is deposited, the thickness of the depletion layer 14 in the $SnO_x$ nanostructure 7 extends on the contrary. In this structure, when a reducing gas is adsorbed on the $SnO_x$ nanostructure 7, since the electric resistance in the $SnO_x$ nanostructure 7 is lowered due to shrinkage of the depletion layer 14 in the $SnO_x$ nanostructure 7, the gas concentration can be sensed by utilizing this phenomenon. Change of the in-plane electric resistance of the gate electrode depending on the absence or presence of gas adsorption is utilized as the principle of sensing.

Figure 6A:
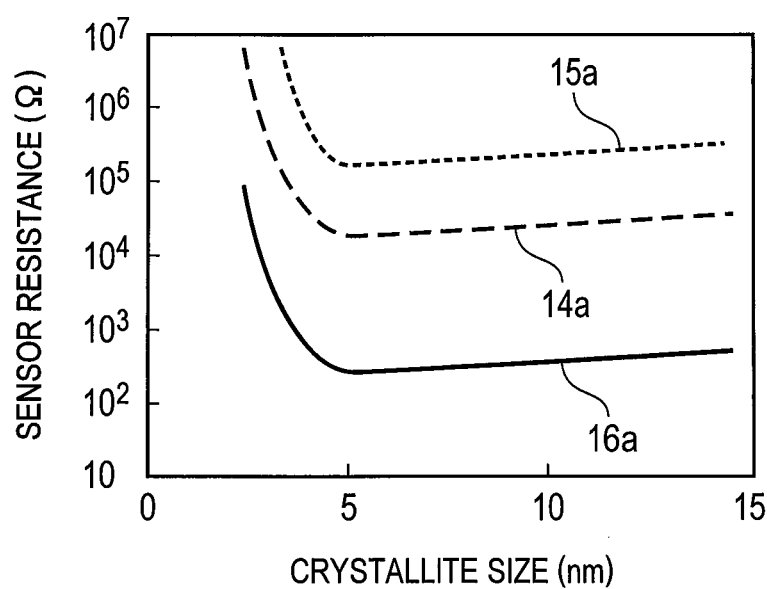
FIG. 6A is a graph showing the dependence of an electric resistance (sensor resistance) on the grain size of a gate electrode having a nano-scaled structure comprising platinum grains and an SnO$_x$ nanostructure and having a resistance-dominant structure of the present invention.

A specific method of preparing a gate structure is to be described later. At first, FIG. 6A shows an example of resistance change in an actual gate structure for an example corresponding to FIG. 2C and FIG. 2D. The data include curves for fitting data when measuring the change of the sensor resistance while changing the grain size of the $SnO_x$ nanostructure (described as crystallite diameter in the drawing). The operation temperature is 250° C. There are shown a sensor resistance $14a$ in air, a sensor resistance $16a$ in 1000 ppm of methane as a reducing gas, and a sensor resistance $15a$ when $NO_2$ is flown at 10 ppm as an oxidizing gas. The crystallite diameter is indicated by an average grain size of the $SnO_x$ nanostructure 7. The sensor resistance increases abruptly at a grain size of 4 nm or less, because the depletion layer shown in FIG. 5B extends from the Pt grain boundaries on both ends and join to abruptly decrease conductive carriers in the $SnO_x$ nanostructure 7 as the grain size is reduced.

Figure 6B:
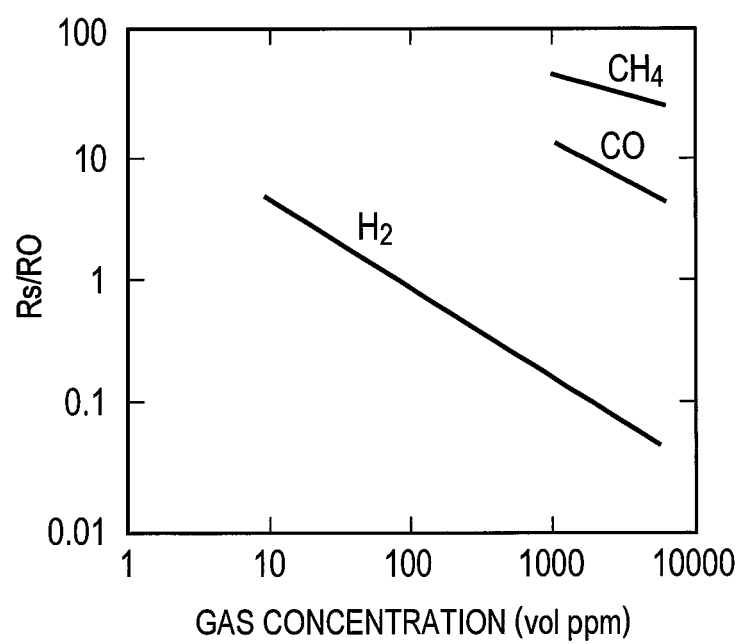
FIG. 6B is a graph showing gas species and gas concentration dependence in a sensor in which a nano-scaled structure comprising platinum grains and an SnO$_x$ nanostructure and having a resistance-dominant structure is applied to a gate electrode of the present invention.

FIG. 6B shows a sensor characteristics to CO, $CH_4$, and $H_2$ gas when the invention is applied to the Si-MOS substrate utilizing the phenomena described above. The sensor operation temperature is 250° C. A reference resistance RO in the response intensity Rs/RO is a ratio relative to the sensor resistance Rs of a gas to be detected, and the graph shows the dependence of the response intensity Rs/RO on the gas concentration with the 100 ppm concentration of a hydrogen gas in air being as a reference.

An existent main stream of gas sensors for CO, $CH_4$, $NH_3$, and NO gas is a sintered type in which a catalyst is carried on a metal oxide at a large film thickness (0.2 to 20 μm). Also in the thin film, by skillfully devising the structure as described above, a long-term reliability and low temperature operation were obtained. In the sintered system, since the inter-grain boundary barrier is high and the contact resistance between the metal oxide grain boundaries is high, it was necessary to set the sensor operation temperature as high as about 400° C.

Then, a manufacturing method of a gate structure described in FIG. 2A and FIG. 2C is to be explained. At first, a method of manufacturing the structure in FIG. 2A is disclosed. After forming a thermal oxide film $SiO_2$ 4 over an Si substrate 5 and forming titanium (Ti) to 10 nm, further, platinum (Pt) to 5 nm by an electron beam vapor deposition (EB vapor deposition) method, they were heated in air at 1 atm, 550° C., for one hour. The thickness of the titanium (Ti) film was 5 nm to 15 nm, the thickness of the platinum (Pt) film was about from 1 nm to 10 nm, and the heating temperature was about 350° C. to 600° C. The thickness of the platinum (Pt) film and the thickness of the titanium (Ti) film used was at a ratio within a range of about 1:1 to 1:5. The heating time was set within a range about from 20 minutes to 2 hours. Further, as the heating atmosphere, air, nitrogen, or argon-diluted oxygen was used. The heating time and the atmosphere were identical also in the following manufacturing methods.

In a second method, by the same method as the method of manufacturing the Pt—Ti—O structure, after at first forming titanium (Ti) to 5 nm and, further, platinum (Pt) to 15 nm by an electron beam vapor deposition (EB vapor deposition) method, they were heated in air at 1 atm, 400° C. for 40 minutes to form a Pt—Ti—O structure. Then, they were heated in air at 1 atm, at 650° C., for 30 minutes to form the structure shown in FIG. 2A. Usually, they were heated at a temperature within a range of about 550° C. to 700° C.

In a third method, after forming a Ti layer to 5 nm by an EB vapor deposition method, Pt and Ti were vapor deposited simultaneously by a co-deposition method at a ratio of Pt and Ti of about 1:3. The film thickness was 15 nm. After the vapor deposition, they were heated in an air atmosphere at 1 atm, 550° C. for 2 hours. In this case, a structure in which Pt grain boundaries were dispersed in titanium oxide was obtained which is different, distinctly, from that of FIG. 2A. The Pt and Ti were used at a ratio within a range about from 1:1 to 1:5. The annealing temperature was within a range about from 400° C. to 650° C.

Then, a method of manufacturing the structure shown in FIG. 2C is disclosed. After forming a thermal oxide film $SiO_2$ 4 over an Si substrate 5, and forming tin (Sn) to 10 nm and, further, platinum (Pt) to 5 nm by an electron beam vapor deposition method, they were heated in an air atmosphere at 1 atm, at 500° C. for one hour. They were usually heated at a temperature from 350° C. to 650° C. The ratio of the thickness of the platinum (Pt) film and the thickness of the tin (Sn) film used was within a range about from 1:1 to 1:5. The heating time was set within a range about from 20 minutes to 2 hours. Further, as the atmosphere during heating, air, nitrogen, or argon-diluted oxygen was used. The heating time and the atmosphere were identical with those in the following manufacturing methods.

In a second method, Pt and Ti were vapor deposited simultaneously by a co-vapor deposition method at a ratio of Pt and Sn of about 1:2. The film thickness was 15 nm. After the vapor deposition, they were heated in air at 1 atm, at 400° C. for 2 hours. The ratio between Pt and Sn was within a range of about 1:1 to 1:5, and heating was usually performed at a temperature of from 350° C. to 650° C.

Successively, a method of manufacturing an Si-MOSFET gas sensor in the first embodiment is to be described. Since the method of manufacturing the Si-MOSFET gas sensor per se has been a well-known technique, the first embodiment is to be described mainly around a step of manufacturing the gate structure as a main feature of the invention and a step of annealing in an oxygen atmosphere. In the first embodiment, an n-channel type MOSFET having a gate length (Lg) of 20 μm and a gate width (Wg) of 300 μm was manufactured. The manufacturing method is to be described with reference to FIG. 7(a).

At first, as shown in FIG. 7(a), local isolation regions 26, 26a are formed to a semiconductor substrate 28 to which a p-type impurity has been introduced. The local isolation regions 26, 26a are formed for defining a gate electrode forming regions, for example, from a silicon oxide film of 250 nm thickness by local oxidation. Then, for forming an re-channel region to the surface of the semiconductor substrate 28, impurities are ion implanted at a dose of $10 \times 10^{11}$ N/cm². Then, ions are implanted for forming an $n^+$-type semiconductor region as a source region 27 and a drain region $27a$ in the semiconductor substrate 28 to form an active layer of an Si-MOSFET.

Successively, after performing a pretreatment to the semiconductor substrate 28 (wafer), a gate insulating film 25 of 18 nm thickness is formed on the surface of the semiconductor substrate 28. The gate insulating film 25 is formed, for example, of a silicon oxide film and can be formed by a thermal oxidation method in an oxygen atmosphere. Then, a gate electrode 20 is formed over the gate insulating film, for example, by a lift off method. The gate electrode 20 comprises a stacked film of a titanium film formed over the gate insulating film 25 and a platinum film formed over the titanium film in this stage. The thickness of the titanium film is, for example, 10 nm, and the thickness of the platinum film is, for example, 5 nm. In this case, $n^+$-type semiconductor regions constituting a source region 27 and a drain region $27a$ are formed conforming to the local isolation region 26 that defines the region for forming the gate electrode 20. Then, the gate electrode 20 is formed so as to cover not only over the gate insulating film 25 but also over the trench of the local isolation region 26 and the ends of the gate electrode 20 are arranged so as to overlap the ends of the $n^+$-type semiconductor region. This is because a technique of forming the $n^+$-type semiconductor region in self-alignment to the gate electrode 20 which is a main stream as a method of forming the Si- MOSFET cannot be used in the first embodiment. The titanium film and the platinum film forming the gate electrode 20 are formed by an electron beam radiation vapor deposition method (EB vapor deposition method) and the deposition rate is 1 Å/s.

The method of forming the titanium film and the platinum film is the EB (electron beam) vapor deposition method. A thin film is formed over the silicon oxide film formed over the silicon substrate. At first, when only the titanium film was formed as the thin film and evaluated, the titanium film of 1 nm to 10 nm thickness was amorphous in which crystal grains are not observed and the surface was uniform and unevenness was scarcely observed. When the thickness of the titanium film was made as thick as 45 nm, most of the film comprises amorphous and titanium metal crystal grains tended to be present partially but the surface was uniform and unevenness was scarcely observed. This is greatly different from the form (morphology) of the platinum film formed over the silicon oxide film formed over the silicon substrate as has been described above.

Then, titanium films of several kinds of film thickness were formed over the silicon film formed over the silicon substrate and a platinum film was deposited by continuous deposition of different film thickness. Also the platinum film was a thin film in which small crystals of fcc (face-centered cubic lattice) crystal structure were oriented in the (111) direction. For the method of forming the gate metal portion, since a great amount of sputtering damages occurred in the gate insulating film and the threshold voltage Vth of FET varied greatly, this is not desirable for the formation of the sensor FET (for example, the threshold voltage Vth of the sensor FET where the gate metal is formed of a sputtered film varies greatly (for example, as shown in FIG. 18 of the prior invention, that is, Japanese Unexamined Patent Application Publication No. 2009-300297 (Patent Literature 1)). Even after an appropriate heat treatment is applied to the scattering, it is difficult to achieve a uniform Vth as in the (EB vapor deposition).

Then, a capacitive gate structure which is a feature of the first embodiment shown in FIG. 2A and FIG. 2B can be achieved by an annealing treatment (heat treatment) at a heat treatment temperature of 550° C. for a heat treatment time of one hour in an air at high purity (oxygen-containing atmosphere).

Figure 7:
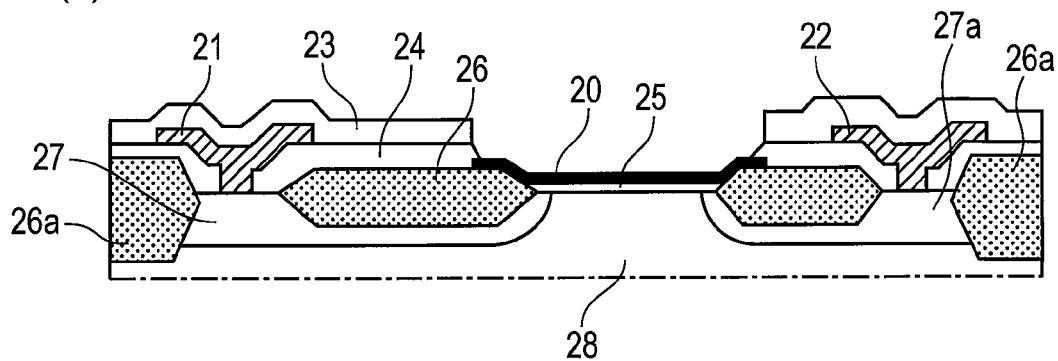
FIG. 7 (a), (b) are views showing steps of manufacturing an Si-MOSFET gas sensor of a first embodiment.
Figure 7:
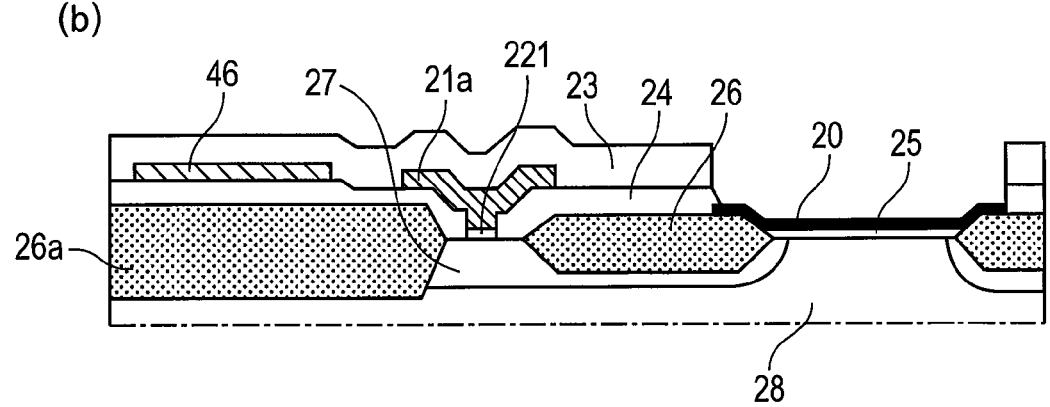

Then, as shown in FIG. 7(*a*), an insulating film 24 comprising PSG (Phosphorus doped glass) is formed over the semiconductor substrate 28 including a portion above the gate electrode 20. Then, a contact hole penetrating the insulating film 24 is formed and subjected to a step such as a surface treatment. The thickness of the insulating film 24 is set to 500 nm. Usually, the thickness of the insulating film 24 is often selected within a range from 400 nm to 1,000 nm. Then, a source electrode 21 and a drain electrode 22 comprising a silicon-containing aluminum (Al) film are formed over the insulating film 24 including the inside of the contact hole. The thickness of the source electrode 21 and the drain electrode 22 is, for example, 500 nm. Although not illustrated in FIG. 7(*a*), an aluminum interconnect formed of the same aluminum film containing silicon as the source electrode 21 and the drain electrode 22 is also formed as a heater for heating a lead electrode of the gate electrode 20 and a chip. The interconnect width of the aluminum interconnect is, for example, 10 μm and the interconnect length is 29000 μm.

Successively, an insulating film 23 that functions as a protective film is formed over the aluminum interconnect over the semiconductor substrate 28. The insulating film 23 is formed, for example, of a silicon nitride film after forming phosphorus-doped glass (PSG) to 200 nm and can be formed by a low temperature plasma CVD method. The thickness of the insulating film 23 is, for example, 700 nm. Finally, opening is formed above an electrode pad (not illustrated) for connection with a bonding wire and an opening portion is formed so as to expose the gate electrode 20 as a sensor portion as shown in FIG. 7(*a*). Thus, the Si-MOSFET gas sensor in the first embodiment can be formed.

While the silicon oxide film is used for the gate insulating film 25 in the first embodiment, an insulating film such as a tantalum oxide ($Ta_2O_5$) film, an aluminum oxide film ($Al_2O_3$) film, or a silicon nitride ($Si_3N_4$) film may also be formed over the silicon oxide film. After the step, a stacked film comprising a titanium film and a platinum film forming the gate electrode may be formed and, subsequently, the Si-MOSFET gas sensor of the first embodiment may be formed by way of the same steps as the steps described above.

Since a great amount of trap levels present in the Ti layer or the gate insulating film (silicon oxide film) are generated, the reproducibility for the uniformity of Vth can be improved by compensating the trap levels by a hydrogen gas of 1000 pp to 1% at a temperature of about 115° C. to 250° C. in the same manner as the Pt-T-O gate hydrogen sensor. By the manufacturing method as described above, the gas sensor characteristics shown in FIG. 4 (already explained) were obtained.

In the Si-MOSFET gas sensor shown in the first embodiment, description has been made to an example of forming the interconnect and the electrode (source electrode 21, drain electrode 22) by using the aluminum film, description is to be made for a modified example of the first embodiment of reliably establishing an ohmic contact with an interconnect using a gold film and silicon with an aim of improving the reliability of the interconnect. In this modified example, the steps up to the formation of the contact hole in the insulating film 24 are identical with those of the first embodiment shown in FIG. 7(*a*).

Successively, a molybdenum film (100 nm), a gold film (500 nm), and a molybdenum film (10 nm) are successively formed over the insulating film 24 including the inside of the contact hole. In this step, the molybdenum film (100 nm) is formed by an EB vapor deposition method and, finally, a gold film (500 nm) and the molybdenum film (10 nm) are formed by a sputtering method. Then, by patterning the stacked films, a source electrode 21*a* (drain electrode 22*a* is not illustrated) and an interconnect 46 shown in FIG. 7(*b*) are formed. Since gold gives an effect of diffusion in silicon at a relatively low temperature, the molybdenum film (100 nm) is used as the barrier metal. In this case, when a heat treatment is applied after forming the interconnect 46, etc., a molybdenum silicide (MoSi) film 221 can be formed as an alloy film of molybdenum and silicon, for example, in a contact region of the source electrode 21*a* and the semiconductor substrate 28. The molybdenum film (100 nm) functions as a barrier film for suppressing diffusion of gold into silicon. The molybdenum film (10 nm) is inserted for improving the adhesion property with the insulating film 23. since the interconnect comprising the molybdenum film (100 nm), the gold film (500 nm), and the molybdenum film (10 nm) is used also for a pad portion, the molybdenum film (10 nm) exposed to the surface is removed upon forming a pad portion. In this case, for connecting a chip and a mounting substrate, a gold wire is used since the bonding by the gold wire improves rust prevention and adhesion property with the pad portion.

Ohmic contact between the source electrode 21*a* and the semiconductor substrate 28 can be established reliably by forming a molybdenum silicide film 221 between the source electrode 21*a* and the semiconductor substrate 28. The structure using the gold film as the interconnect material is more expensive compared with a structure using an aluminum film as the interconnect material, but this is excellent in the humidity resistance or oxidation resistance. As described above, interconnect materials can be used selectively such that a gold film is used for the interconnect with a view point of ensuring the reliability of the interconnect, and an aluminum film is used for the interconnect with a view point of decreasing the cost.

As has been described above, in the first embodiment, while the description has been made to the Si-MOSFET gas sensor in which the titanium film is formed in a layer below the platinum film forming the gate electrode during the manufacturing step, it will be apparent that, instead of the titanium film, tin (Sn), indium (In), Iron (Fe), cobalt (Co), tungsten (W), molybdenum (Mo) film, tantalum (Ta) film, niobium (Nb) film, chromium (Cr), nickel (Ni) film, etc. may also be used in addition to Ti, and a gas sensor of high reliability and high sensitivity can be formed by the same method as explained for the first embodiment.

Second Embodiment

A second embodiment discloses an example for a resistance-dominant structure shown in FIG. 2C and FIG. 2D. Since the preparation method for the gate portion in the second embodiment has been described in the disclosure for the first embodiment, a method of manufacturing a gas sensor prepared over an Si-MOS structure in the second embodiment is to be described. Those portions in common with the first embodiment and the second embodiment are not referred to specifically and description is to be made on those having a direct concern with the second embodiment. In the second embodiment, the gate structure comprises a gate electrode having a gate length (Lg) of 20 μm and a gate width (Wg) of 3000 μm and formed in an accordion-fold pattern over the MOS structure like in the first embodiment. The manufacturing method is to be described with reference to FIG. 8($a$) to FIG. 8($c$). Among the reference sings described in FIG. 8($a$) to FIG. 8($c$), the reference signs identical with those in FIG. 7($a$) and FIG. 7($b$) show the same constituent elements.

Figure 8:
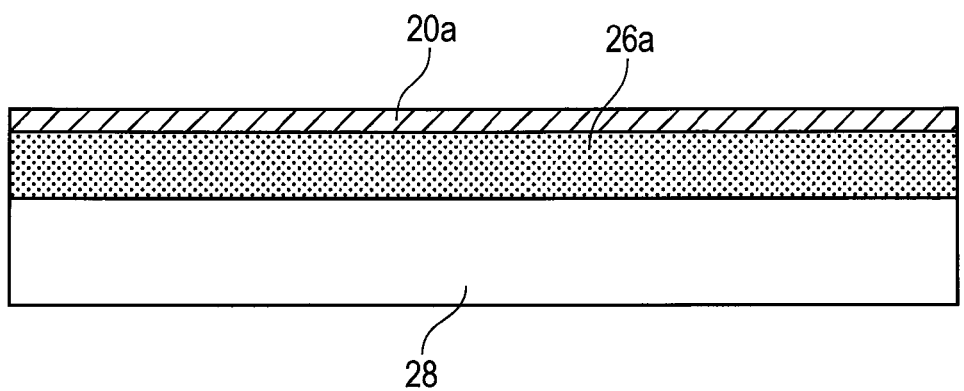
FIG. 8 (a, (b), (c) are views showing steps of manufacturing an Si-MOS gas sensor in an second embodiment.
Figure 8:
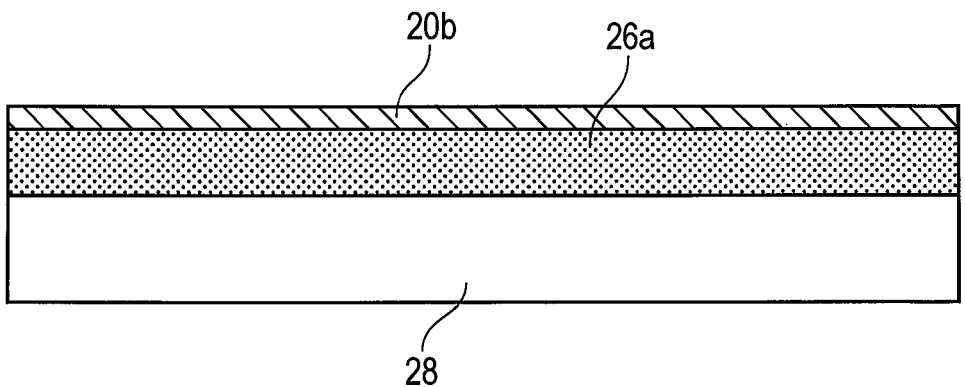
Figure 8:
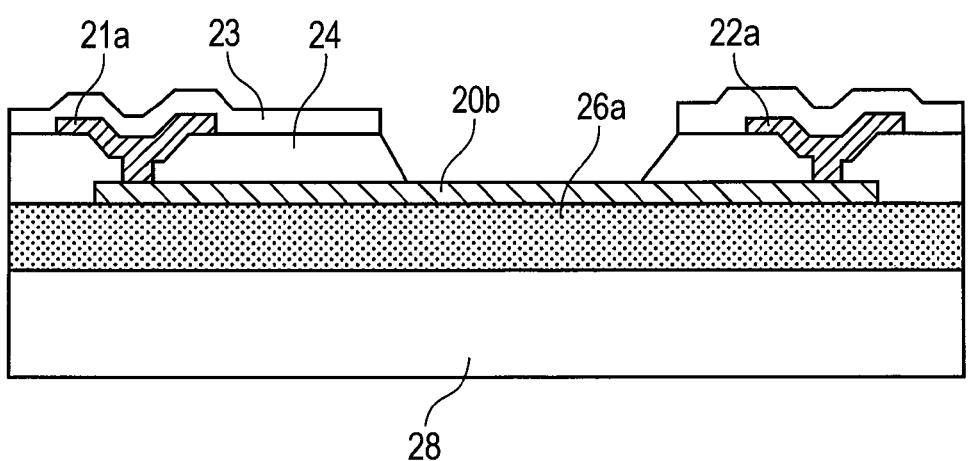

At first in FIG. 8($a$), after applying a pretreatment to a semiconductor substrate 28 (wafer), an insulating film 26$a$ of 124 nm thickness is formed to the surface of the semiconductor substrate 28. The insulating film 26$a$ comprises, for example, a silicon oxide film and can be formed by a thermal oxidation method in an oxygen atmosphere. Then, a stacked film 20$a$ comprising a tin film and a platinum film is formed over the entire surface of the semiconductor substrate 28 by an EB vapor deposition method under irradiation of an electron beam. In this case, the thickness of the tin (Sn) film is 5 nm and the thickness of the platinum film is 3 nm. The film deposition rate of the titanium film and the platinum film is 1 Å/s.

Then, as shown in FIG. 8($b$), an annealing treatment is applied at a heat treatment temperature of 500° C. for a heat treatment time of 60 minutes in an air at high purity to transform the stacked film 20$a$ into a thin film 20$b$. The thin film 20$b$ has the structure shown in FIG. 2C and FIG. 2D. When a dummy solid film formed under the same conditions as those for forming the thin film 20$b$ was evaluated by X-rays, the thin film was changed into a structure where amorphous tin doped with oxygen at a high concentration is mixed slightly to tin oxide. Then, as shown in FIG. 8($c$), the gate electrode 20$b$ and a lead-out electrode (not illustrated) are left by photolithography and, on the other hand, unnecessary platinum and tin oxide films are removed by an ion milling method. When the electroconductivity is extremely low, the tin oxide film may be left as a surface protective film but, in the second embodiment, unnecessary tin oxide film in the region other than region for forming the gate electrode 20$b$ is removed. Thus, a gate structure shown in FIG. 2C can be obtained.

Then, as shown in FIG. 8($c$), an insulating film 24 comprising PSG (phosphorus doped glass) is formed over a semiconductor substrate 28 also including a portion above the gate electrode 20$b$. Then, a contact hole penetrating the insulating film 24 is formed and subjected to a step such as a surface treatment. Then, a lead electrode 21$a$ and a lead electrode 22$a$ comprising a silicon-containing aluminum (Al) film are formed over the insulating film 24 also including the inside of the contact hole. The film thickness is, for example, 500 nm. Although not illustrated in FIG. 8($c$), an aluminum interconnect formed of the same silicon-containing aluminum film as the lead-out electrode 21$a$ or the lead-out electrode 22$a$ is also formed as a heater for heating the lead-out electrode of the gate electrode 20$b$ or the chip. The interconnect width of the aluminum interconnect is, for example, 20 μm and the interconnect length thereof is 29000 μm.

Successively, an insulating film 23 that functions as a protective film is formed over the aluminum interconnect above the semiconductor substrate 28. The insulating film 23 is formed of a silicon nitride film after forming PSG to 200 nm and can be formed by a low temperature plasma CVD method. The thickness of the insulating film 23 is, for example, 700 nm. Finally, an opening is formed over an electrode pad (not illustrated) for connection with a bonding wire, and an opening is formed so as to expose the gate electrode 20$b$ as a sensor portion as shown in FIG. 8($c$). As described above, a resistance-dominant gas sensor according to the second embodiment can be formed. Specific examples of gas response have already been described with reference to FIG. 6B.

In the same manner as the modified example of the first embodiment, a gas sensor in which an interconnect is formed of a stacked structure comprising Mo/Au/Mo is also formed.

In the second embodiment, while the silicon oxide film is used for the insulating film 26, an insulating film, for example, a tantalum oxide ($Ta_2O_5$) film, an aluminum oxide ($Al_2O_3$) film, or a silicon nitride ($Si_3N_4$) film may also be formed over the silicon oxide film as in the first embodiment.

Also in view of the result of FIG. 6B, the second embodiment is applicable as a hydrogen gas sensor in a low concentration region.

Third Embodiment

Figure 9:
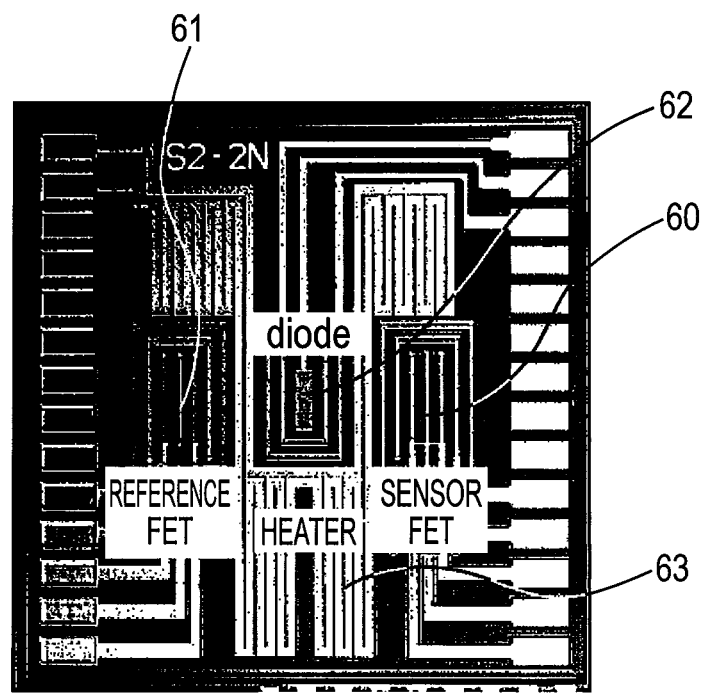
FIG. 9 is an optical microscopic photograph of a semiconductor chip forming a hydrogen gas sensor in a third embodiment.

Then, a configuration of a hydrogen gas sensor of a third embodiment applicable to a high concentration region from about 1% to about several tens % is to be described. FIG. 9 is an optical microscopic photograph of a semiconductor chip in which an hydrogen gas sensor of a third embodiment is formed. As shown in FIG. 9, a sensor FET 60, a reference FET 61, a heater 63 comprising a metal interconnect, and a pn junction diode 62 for measuring a chip temperature are formed over a 2 mm×2 mm sized semiconductor chip (silicon chip) CHP. In this case the interconnect heater has an interconnect width of 30 μm and an interconnect length of 19000 μm. For the sensor FET 60 and the reference FET 61, the Si-MOSFET described in the first embodiment is used. Description is to be made mainly for the configuration of the sensor FET 60 and that of the sensor FET 61, which are basically different from that of the first embodiment.

The hydrogen gas sensor in the third embodiment can be achieved by the improvement in a Pt—Ti—O gate MOS hydrogen sensor. That is, instead of a Pt (15 nm)/Ti (5 nm)/

SiO$_2$ (18 nm)/Si stacked film MOS structure, a hydrogen sensor durable for long-term reliability with the lower limit of hydrogen concentration at 1000 ppm and the upper limit of hydrogen concentration at 70 to 90% could be achieved by increasing the thickness of the Pt layer from 30 nm to 45 nm and applying annealing in air at 400° C. for about 2 hours to 120 hours and annealing at 115° C. to 350° C. in 1000 ppm to 1% air-diluted hydrogen gas. For the reason in view of the structure, while the platinum grain boundary is longer and the annealing time in air increases for forming a hydrogen corridor 77a where titanium and oxygen are agglomerated, the structure shown in FIG. 1B is achieved basically, even hydrogen atoms with small atom size is difficult to pass the hydrogen corridor 77a, and the sensing response concentration is greatly shifted toward high concentration side.

Figure 10:
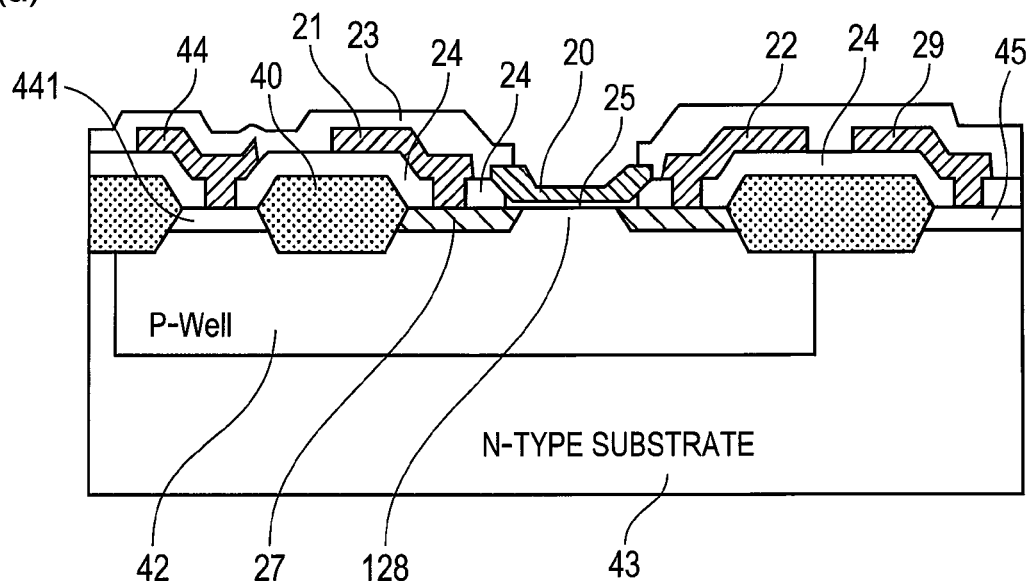
FIG. 10 (a) is a view showing a cross sectional structure of a sensor FET formed over an n-type semiconductor substrate in a fourth embodiment. (b) is a view showing a cross sectional view of a reference FET formed over an n-semiconductor substrate.
Figure 10:
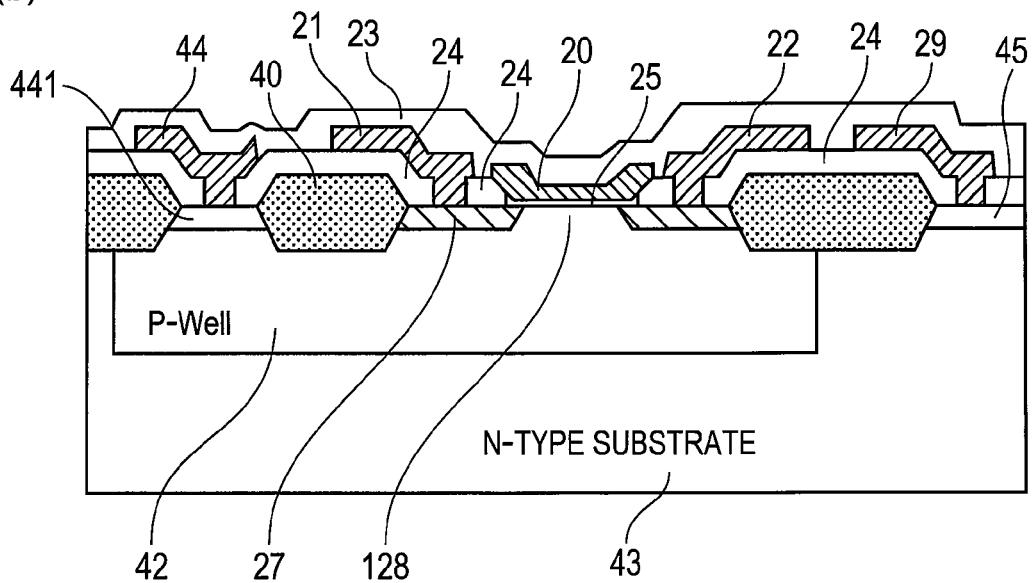

In the hydrogen gas sensor of the third embodiment, since two types of FETs (sensor FET 60 and reference FET 61) and the PN-junction diode 62 are integrated over a semiconductor chip, device isolation is necessary for isolating the devices. In the third embodiment, a well-known PN-junction isolation technique is used for isolating the devices from each other. FIG. 10(a) shows a cross sectional structure of the sensor FET 60 formed over an n-type semiconductor substrate and FIG. 10(b) shows a cross sectional structure of the reference FET 61 formed over the n-type semiconductor substrate. Among the reference signs described in FIG. 10(a) to FIG. 10(b), the reference signs identical with those in FIG. 7(a) show identical constituent elements.

As shown in FIG. 10(a), a p-type well 42 for defining a region forming the sensor FET is formed in the n-type semiconductor substrate 43. The p-type well 42 comprises, for example, a p-type semiconductor region formed by an ion implantation method. In this case, for fixing the potential of the p-type well 42, a p$^+$-type semiconductor region 441 is formed to the n-type semiconductor substrate 43, for example, by an ion implantation method. Then, a p-type well 44 formed of the same aluminum film as the source electrode 21 or the drain electrode 22 is formed so as to be connected with the p$^+$-type semiconductor region 41. In the same manner, for fixing the potential of the n-type semiconductor substrate 43, an n$^+$-type semiconductor region 45 is formed to the semiconductor substrate 43, for example, by an ion implantation method. Then, a substrate electrode 29 formed of an aluminum film is formed so as to be conducted with the n$^+$-type semiconductor region 45.

As shown in FIG. 10(b), a p-type well 42 for defining a region for forming the reference FET is formed in the n-type semiconductor substrate 43 also for the reference FET 61. The p-type well 42 comprises, for example, a p-type semiconductor region formed by an ion implantation method. In this case, for fixing the potential of the p-type well 42, a p$^+$-type semiconductor region 41 is formed to the n-type semiconductor substrate 43, for example, by an ion implantation method. Then, a p-type well electrode 44 formed of the same aluminum film as the source electrode 21 and the drain electrode 22 is formed so as to be connected with the p$^+$-type semiconductor region 441. In the same manner, for fixing the potential of the n-type semiconductor substrate 43, an n$^+$-type semiconductor region 45 is formed to the semiconductor substrate 43a, for example, by an ion implantation method. Then, a substrate electrode 29 formed of an aluminum film is formed so as to be connected with the n$^+$-type semiconductor region 45.

The sensor FET 60 and the reference FET 61 configured as described above are different in that the gate electrode 20 is exposed from the insulating film 23 in the sensor FET 60, whereas the gate electrode 20 is covered with the insulating film 23 in the reference FET 61. They are different since it is necessary for the sensor FET 60 to be in contact with a hydrogen gas, whereas the FET 61 is configured so as not to be in contact with the hydrogen gas.

While the cross sectional view of the PN-junction diode (not illustrated) is not shown, the junction area is 60 μm×200 μm. It is found in view of the temperature calibration condition that the state in which a current at 10 μA flows at a rising voltage: Vf=0.3 V of a forward bias which is diode characteristics corresponds to the chip temperature at 100° C.

For the interconnect of the hydrogen gas sensor in the third embodiment, for example, an Mo/Au/Mo structure is adopted. In the same manner, the Mo/Au/Mo structure is adopted also for the heater wiring and the source electrode 21 and the drain electrode 22. On the other hand, an experimental product of using an aluminum interconnect used in the first embodiment for the heater wiring and the source electrode 21 and the drain electrode 22 is also manufactured. In the third embodiment, a reliability test is performed by using two types of the interconnect materials. As a result, while a gold interconnect shows a longer life in a high temperature heat acceleration test and a high temperature high humidity test compared with the aluminum interconnect, the manufacturing cost becomes expensive, so that they should be used selectively depending on the applied products.

After forming the gate electrode, an interconnect is formed over the insulating film 24, and an insulating film (PSG) film and an insulating film (silicon nitride film) 23 are formed over the entire surface of the semiconductor substrate covering the interconnect. Subsequently, in the region for forming the sensor FET 60, the insulating film 23 over the gate electrode 20 (sensor sensing portion) comprising the platinum film is removed to form the sensor FET 60. On the other hand, in the region for forming the reference FET, the insulating film 23 over the gate electrode 20 comprising the platinum film is left without removal. With such a configuration, a substantially identical threshold voltage: Vth=1.02 V is obtained in both of the sensor FET 60 and the reference FET 61.

If only the sensor FET 60 is formed alone, the annealing treatment performed in air at high purity, at an annealing temperature of 400° C. for an annealing time from 2 hours to 120 hours may not be performed in the course of the manufacturing steps of the gas sensor and the annealing treatment may also be performed at the instance the manufacturing step for the gas sensor have been completed. By the annealing treatment (heat treatment), since the dominant factor for Vth by the work function of titanium before the heat treatment changes to the dominant factor for Vth by the work function of platinum, the threshold voltage Vth is decreased by about 1.2 V.

However, when it is intended to integrate also the reference FET 61 simultaneously to the semiconductor chip CHP and align the threshold voltage Vth with that of the sensor FET 60, since the insulating film 24 and the insulating film 23 protecting the gate electrode 20 of the reference FET 61 do not allow oxygen to permeate therethrough, the initial titanium work function remains as the dominant factor of the threshold voltage Vth for the threshold voltage Vth of the reference FET 61.

Fourth Embodiment

While description has been made in the first embodiment to the fourth embodiment for the examples applied to the gas sensor of MOS structure, the present invention can be achieved also by using an MIS capacitor or a Schottky diode. Particularly, for the MIS capacitor, the planar shape of the gate electrode 20 may be formed, for example, to a circular shape of 50 μm to 100 μm diameter and the source electrode 21 and the drain electrode 22 may be formed to a shape concentrically surrounding the gate electrode 20 in FIG. 7(a) explained for the first embodiment. In the MIS capacitor, gas response can be measured, for example, by defining the voltage in a flat band state as a threshold voltage Vth. In the MIS capacitor, the gate electrode 20 functions as an upper electrode, and the semiconductor substrate 28 just below the gate electrode functions as a lower electrode. Then, when the semiconductor substrate 28 is configured to be electrically connected with the source electrode 21 and the drain electrode 20, the lead electrodes for the lower electrode serves as the source electrode 21 and the drain electrode 22.

Further, the gate insulating film 25 between the gate electrode 20 and the semiconductor substrate 28 serves as a capacitive insulating film. The thus configured MIS capacitor utilizes the phenomenon that the channel region formed on the surface of the semiconductor substrate 28 is formed or eliminated depending on the presence or absence of an ammonia gas, a CO gas, a methane gas, a hydrogen gas, an NO gas and, further, an $NO_2$ gas (corresponding to the change of the threshold voltage Vth depending on the hydrogen gas). That is, since the electric capacitance of the MIS capacitor changes depending on the presence or absence of the channel region formed in the semiconductor substrate 28, presence of a gas can be detected indirectly by detecting the change of the electric capacitance.

While the examples described above (first to third embodiments) show examples of applying the invention to sensors for the ammonia gas, the CO gas, the methane gas, the hydrogen gas, NO gas and, further, $NO_2$ gas, etc. applied to the Si MOS structure, the present invention is applicable also to devices using other semiconductor materials, for example, silicon carbide (SiC), gallium arsenide (GaAs), gallium nitride (GaN), etc., that is, applicable also to MIS FET, MIS capacitor, Schottky gate FET, PN-junction gate FET using such semiconductor materials.

Fifth Embodiment

A fifth embodiment concerns means for solving the seventh subject.

At first, description is to be made to means for solving the seventh subject.

This embodiment is an actual example of an embodiment concerning the low consumption power and heat insulation characteristics for the sensor region and the peripheral portion in the first embodiment and the second embodiment.

Low consumption power for the Si-MOSFET gas sensor can be achieved by heat insulation by decreasing the surface area of the heater region to decrease heat dissipation from the surface of the heater region and insulating heat diffusion of the heater region by adopting an MEMS structure to be described below. A basic concept for solving the subject (low consumption power and heat insulation for the periphery) according to the fifth embodiment is as described below.

The upper limit for the operation temperature of Si-MOSFET is at about a sensor operation temperature of 150° C. and the gas sensor of the first embodiment was applied to the MEMS gas sensor taking notice on whether the heat insulation characteristics at the peripheral portion is sufficient or not and when extent of the consumption power can be decreased at a sensor operation temperature of 215° C. as the lower limit for the operation temperature of the resistance-dominant of MOS structure sensor. Since the thermal design is substantially identical also in the resistance-dominant form, it is substituted by the gas sensor of the first embodiment is used as a substitute.

(1) Since the heat efficiency is poor and the thermal capacity increases excessively, if the sensor chip is entirely heated to 100 to 150° C., the thermal capacity of the intrinsic FET region is decreased to $\frac{1}{1000}$ or less of the existent case, thereby decreasing the temperature elevation rate to several tens of milliseconds or less even in low consumption power.

(2) In order to decrease the heat dissipation from the surface of the heater region into an atmospheric gas, a structure of inserting a heater wiring into gap portions between the source electrode and the gate electrode and between the drain electrode and the gate electrode respectively is adopted thereby decreasing the surface area of the heater region, for example, to 300 μm×300 μm or less.

(3). The thermal resistance of the lead-out interconnect from the intrinsic FET region to the pad electrode is made larger only with slight increase in the parasitic resistance of the sensor FET.

(4) In order to prevent thermal release from the mounting lead wire, the number of the lead wires is set to four, the diameter of the mounting lead wire is 8 to 25 μm, and the length thereof is set to about 3 to 12 mm.

(5) In order to prevent thermal release through the heat insulation material inserted between the sensor chip and the mounting substrate (stem pedestal), a foamed glass heat insulator having an extremely low thermal conductivity is used.

(6) According to (1) to (5) described above, a gas sensor of low consumption power of about 25 to 0.3 mW is achieved in a case of battery operation at a voltage of 3 V.

In the Si-MISFET gas sensor, it is necessary that only the portion of a catalyst metal gate that controls the channel of the sensor FET is kept at a predetermined temperature. Since the temperature of the sensor chip can be measured when the temperature characteristics of the resistance of the heater wiring is known, the resistance value of the heater wiring can be used as a thermometer.

Accordingly, since the PN-junction diode for measuring the chip temperature is not always necessary in the sensor chip, the area of the sensor chip can be decreased by removing the PN junction diode. The area of the sensor chip can be decreased by incorporating only the sensor FET into the chip and the area of the heat source (heat wiring) can be decreased since it may suffice that only the catalyst metal gate of the sensor FET may be heated. Accordingly, the consumption power can be decreased.

Further, since the number of the mounted lead wires can be decreased, for example, to four, heat dissipation from the mounted lead wires can be prevented. It may suffice that the temperature of the catalyst metal gate of the sensor FET can be maintained at a predetermined temperature of 150 to 215° C., and the temperature is lowered compared with the operation temperature 400° C. of a typical gas sensors.

In view of the above, in the fifth embodiment, an SOI substrate is adopted at first, an Si substrate for the portion of the sensor FET of the SOI substrate is bored as far as the filled insulation layer (MIMS region) and a meandering heater wiring is disposed in a gap between the source electrode and the catalyst metal gate and in a gap between the drain electrode and the catalyst metal gate (heater region). Thus, since the heater region is decreased compared with other heating structures for the heater arrangement that heats the sensor FET entirely, the heat flow from the surface of the heater region to the atmospheric gas can be decreased and, further, arrangement of the catalyst metal gate to the heater region simplifies the production process.

The regions including the catalyst metal gate, the source electrode, and the drain electrode of the sensor FET, and the heater region described above are hereinafter referred to as an intrinsic FET region.

Further, by adopting a structure of where the intrinsic FET region does not overlap the MEMS region is formed, and the thermal resistance of the insulation thin film covering the region is increased, thereby providing a structure that the heat of the heater region heated by the heater wiring does not escape to the periphery (thermally insulated, adiabatic structure). Further, the sensor chip is disposed over a heat insulating material of high thermal resistance, a lead-out wiring is disposed so as not to increase the effect of the thermal resistance of the lead-out wiring as far as the mounting lead wires on the electric resistance of the sensor FET or the heater wiring, and the thermal resistance of the mounting lead wires is increased thereby providing the adiabatic structure for thermal dissipation from the heater region to the mounting substrate (stem pedestal). Thus, a low consumption power sensor of 25 to 0.3 mW is achieved.

Further, a region where the intrinsic FET region and the MEMS region do not overlap is formed and several through holes are formed in the insulating thin film for further increasing the thermal resistance of the insulating thin film covering region.

If the MEMS region is excessively large, the mechanical strength of the MEMS region is degraded to impair long-term reliability. Then, degradation of the mechanical strength of the MEMS region can be prevented by connecting the intrinsic FET region and the outside of the MEMS region by using a lead-out wirings for the heater wiring, and lead-out wirings for the source electrode, the drain electrode, and the catalyst metal gate of the sensor FET are provided in addition to a reinforcing region formed by leaving the insulating thin film in a region where the intrinsic FET region and the MEMS region do not overlap.

Further, the structure of preventing the heat of the heater region from escaping to the periphery (heat insulated, adiabatic structure) is achieved by making the thermal resistance of regions where the intrinsic FET region and the outside of the MEMS region is connected by the lead-out wirings described above. (hereinafter referred to as bridge region) equal with or less than the thermal resistance of the insulating thin film covering the region where the intrinsic FET region and the MEMS region do not overlap.

In the fifth embodiment, the nearest distance between the intrinsic FET region and the MEMS region is formed as large as 1 to 20 times compared with the sum of the width for the bridge region and the width of all of the reinforcing regions.

Constitutional conditions and operation conditions of the sensor chip for achieving the means capable of solving the subject are to be summarized.

It is considered that the temperature of the stem portion is identical with the environmental temperature Te and the convection effect of air on the heat dissipation from the heater surface is neglected. The entire thermal resistance Rth of the system is as described below. The thermal resistance accompanying thermal dissipation from the surface of a heater region into an atmospheric gas as $R_A$. The thermal resistance path along with heat dissipation from the surface of the heater region into the atmospheric gas is defined as $R_A$, and the thermal resistance path from the heater to air below the MEMS, the heat insulation material and the stem (thermal resistance $R_D$) is generally classified into three paths, that is, a path from the heater to the edge of the MEMS region (thermal resistance $R_M$), a path from the edge of the MEMS region edge through the Si substrate to the heat insulation material and the stem (thermal resistance $R_S$), and a path to the surface of the Si crystal, the lead wire, the pin electrode, the and stem (thermal resistance $R_1$).

The thermal resistance along with thermal dissipation from the surface of the heater region into the atmospheric gas is defined as $R_A$. Then, assuming the radius of a circle having an identical area with the surface area of the heater region as $r_A$ and thermal conductivity of air at a temperature of the heater wire as $\lambda$, the thermal resistance $R_A$ can be approximated by using the thermal resistance $1/(4\pi\lambda \cdot r_A)$ from the circular heating body having radius $r_A$. Further, since the thermal resistance $R_S$ and the thermal resistance $R_M$ are arranged in parallel and arranged in series with the thermal resistance $R_M$, it is considered that the temperature for the stem portion is identical with the environmental temperature Te and air convection effect on the thermal release from the surface of the heater is neglected. The entire thermal resistance $R_{th}$ of the system includes three types of parallel circuits described above and can be represented as:

$$1/R_{th}=1/R_D+1/R_P+1/R_A \qquad \text{formula (2)}$$

$$R_D=R_D(\text{air})+R_D(\text{heat insulation material}) \qquad \text{formula (2-1)}$$

$$R_P=R_M+R_S \cdot R_L/(R_S+R_L) \qquad \text{formula (2-2)}$$

$$R_A=1/(4\pi\lambda r_A) \qquad \text{formula (2-3)}$$

$R_D$ (air) is a thermal resistance for a portion of air below the MEMS region, and $R_D$ (heat insulation material) is a thermal resistance of the heat insulation material below the MEMS region. $R_S$ is a thermal resistance from the silicone chip other than the MEMS region to the stem and this is effectively a thermal resistance of the heat insulation material other than the MEMS region.

Therefore, when it is assumed that a temperature difference between the set temperature Ts of the heater region and the environmentally-assumed lowest temperature Temin upon installation of the gas sensor is represented as $\Delta$Tmax (=Ts−Temin) and that a heater maximum power charged to the heater wiring which is determined by the electric resistance R(Ts) of the heater wiring at the set temperature Ts and the power source voltage Vdd to be used is represented as "Powmax", a required condition is to set the thermal resistances $R_D$ and $R_P$ and the surface area of the heater region, at the heater maximum power Powmax of 25 mW or less, so as to satisfy:

$$\text{Powmax}/\Delta T\text{max}>1/R_D+1/R_P+4\pi\lambda \cdot r_A \qquad \text{formula (3)}$$

The environmentally-assumed lowest temperature Temin upon installation of the hydrogen gas sensor is about −65° C. and, in the case of the Si-MISFET-type gas sensor, in the operation at a temperature of 150° C. which is a chip temperature at the highest limit, the set temperature Ts of the heater region may be considered substantially as the operation temperature of 15° C. Therefore, in this case, the temperature difference $\Delta$Tmax becomes 215° C. (=Ts−Temin).

Further, since the thermal capacity of the heater region can be decreased by three digits or more by adopting such an MEMS structure, the arrival time t0 for an increase rate, a decrease rate of a temperature, etc. can be decreased. Therefore, the structure is suitable to the intermittent operation of the heater wiring and since the duty ratio $(\tau_1/(\tau_1+\tau_2))$ can be decreased, for example, to about $\frac{1}{14}$ as described below, the consumption power can be effectively decreased by one digit or more compared with that in the continuous operation. Practically, in the case of the flammable gas, the duty ratio is in a range from $\frac{1}{14}$ to 1.0.

The heater maximum power Powmax is determined by the power source voltage Vdd (3 V in the case of the gas sensor operated by two lithium cells having a current capacity of 2.6 Ah) and the electric resistance R(Ts) of the heater wiring at the set temperature Ts. Actually, when the electric resistance R(Ts) of the heater wiring is set to an excessively high level, the heater maximum power Powmax becomes too small. When the temperature difference ΔT is set to be excessively large by increasing the operation temperature of the gas sensor, there is no actual combination of the thermal resistances $R_D$ and $R_P$ and the surface area of the heater region that satisfies the formula (3). Therefore, in the case of the gas sensor, as the heater maximum power Powmax is decreased, it becomes significantly difficult to achieve the structure capable of providing the temperature difference ΔT=215° C. and the operation chip temperature of 150° C.

On the other hand, as the heater power Pow is increased, it is necessarily easy to obtain the actual combination of the thermal resistances $R_D$ and $R_L$ and the surface area of the heater region which satisfies the formula (3). However, since the response speed within 30 seconds is necessary in the case of the gas sensor, the duty ratio is limited. Therefore, the heater power Pow cannot be increased needlessly, and an upper limit of the heater maximum power Powmax becomes 25 mW as described below. In a case of the Si-MISFET-type gas sensor according to the first embodiment, since a response speed close to one second is shown in a region of a gas concentration from 1000 ppm to several %, a lower limit of the duty ratio can be decreased to about 1/14. Since the upper limit of the consumption power in the continuous operation which can ensure the operation for one year by using two lithium cells is 1.78 mW, the upper limit of the consumption power which allows the operation for one year by two lithium cells is about 25 mW in view of: 25 mW×1/14≈1.78 mW. Therefore, the maximum consumption power which can make the cell capacity and the safety for the flammable gas detection compatible is about 25 mW.

In an actual structure, there is a thermal resistance $R_M$ of a thermal flow flowing in the bridge region that connects the intrinsic FET region and the outside of the MEMS region. As the thermal resistance $R_M$ decreases, an effective heater region is increased, so that the thermal resistance $1/(4\pi\lambda \cdot r_A)$ is decreased and the formula (3) is no more satisfied. That is, even if the power is charged to the heater wiring, the chip temperature does not reach the set temperature Ts. However, when the thermal resistance $R_M$ is set such that a temperature difference between the intrinsic FET region and an edge of the MEMS region or the pad electrode is about 50% or more of the temperature difference ΔTmax, thermal diffusion from the heater region to the thin film at the periphery or the substrate can be prevented.

Since the degree of freedom of a configuration to the thermal resistances $R_D$, $R_L$, and $r_A$ is high, a structure of the gas sensor which satisfies the Formula (3) can be achieved in a region from 25 to 0.3 mW.

Incidentally, when it is intended to decrease the consumption power while fixing the temperature of the catalytic metal gate used for the Si-MISFET-type flammable gas sensor as it is, for example, at 150° C., it is required to decrease a cross-sectional area of the heater wiring to increase the heater resistance. However, when the density of a current flowing in the heater wiring is excessively high, a problem such as disconnection arises for the reliability and, therefore, the cross-sectional area of the heater wiring cannot be decreased needlessly. Therefore, instead of a heater wiring comprising Al or Au having a low resistivity, WSi, W, polysilicon (polycrystal silicon), or the like having a high resistivity is used. In this manner, since the cross-sectional area of the heater wiring can be maintained to such an extent that the problem for the density of the current described above can be avoided and a length of the heater wiring can be further decreased, the surface area of the heater region is decreased as a result to further reduce the consumption power.

In the fifth embodiment, application of an n-channel type MISFET to the sensor FET is to be explained. In the gate structure of the sensor FET, the gate length and the gate width, and the planar shape are identical with those of the first embodiment.

Next, a structure of the Si-MISFET-type gas sensor according to the first embodiment to which the structure condition and the operation condition of the sensor chip for achieving the means to solve the subject described above is to be explained in details.

Figure 11A:
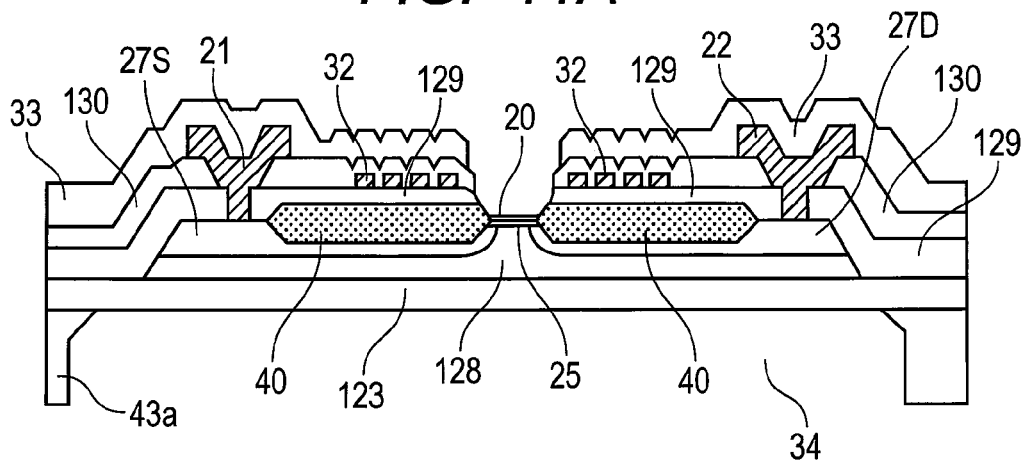
FIG. 11A is a cross sectional view for a main portion of an MISFET used for a sensor according to a fifth embodiment of the present invention.
Figure 11B:
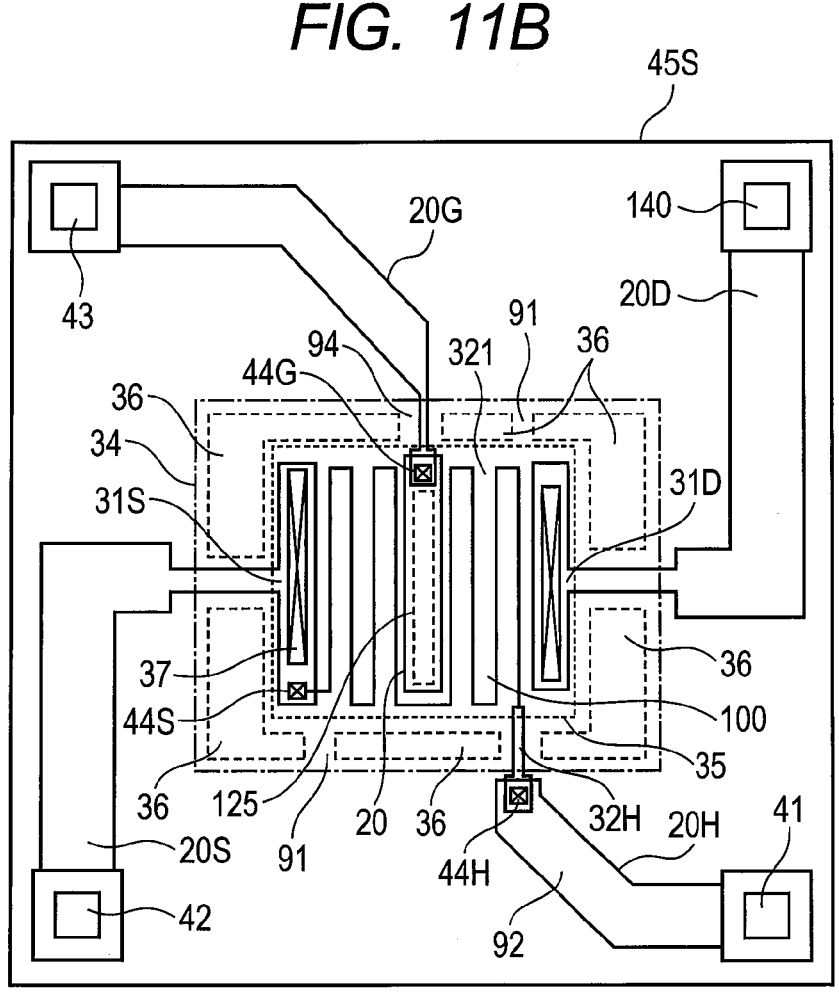
FIG. 11B is a planar view for a main portion of a sensor chip according to the fifth embodiment of the present invention.

First, the sensor chip is to be explained with reference to FIGS. 11A, 11B, and FIGS. 11C, 11D. FIG. 11A illustrates a principal part of a sensor FET, a heater wiring, a lead-out wiring, etc. formed on an SOI substrate. FIG. 11B illustrates the principal part of the sensor chip, the heater wiring, the lead-out wiring, the pad electrode, etc. formed on the SOI substrate. As illustrated in FIG. 11A, a filled insulation layer ($SiO_2$ layer) 123, a channel layer (Si layer) 128, $n^+$-type Si layers 27S and 27D, a gate insulating layer ($SiO_2$ film) 25, a gate electrode (catalytic metal gate) 20, a source electrode 21, a drain electrode 22, etc. are formed on an Si substrate 43a. The gate length of the electrode gate 20 is, for example, 5 μm and the gate width thereof is, for example, 20 μm. The thickness of the channel layer 128 is, for example, 0.1 to 5 μm. and a typical thickness thereof can be exemplified as 0.2 μm. The thickness of the filled insulation layer 123 is in a range, for example, of 0.1 to 5 μm, and a typical thickness thereof can be exemplified as 3 The thickness of the Si substrate 43a is, for example, 200 to 750 and a typical thickness thereof can be exemplified as 500 μm.

Further, since the thermal conductivity $\lambda$, of the Si crystal is decreased by doping, if the heat insulation is desired as in the fifth embodiment, a p-type Si substrate formed by adding high-concentration p-type impurities into the Si substrate 43a is used. Thus, since the thermal conductivity A, is decreased to about 1/3 of that of the Si crystal to which the impurities are not added, the heat insulation property is improved. In the fifth embodiment, while a p-type Si substrate formed by adding B (boron) into the Si substrate 43a is used, a high-concentration SOI substrate can also be used.

In the fifth embodiment, after forming the $n^+$—Si layers 27S and 27D by an ion-implantation method, they are subjected to thermal annealing treatment for activation, in which a local oxidation film ($SiO_2$ film) 40 is formed by propagative oxidation in the thermal annealing treatment. After forming the $n^+$-type Si layers 27S and 27D below the local oxidation film 40, the $n^+$-type Si layers 27S and 27D and the channel layer 128 are selectively removed except for an intrinsic FET region 35 in which the source electrode 21, the drain electrode 22, and the principal part of the gate 20 for the sensor FET are formed. This procedure is intended for thermally insulating the intrinsic FET region 35 efficiently because, when the area of the channel layer 128 is large, heat flown into the intrinsic FET region 35 heated by the heater wiring 32 tends to escape to the surroundings since the thermal conductivity of the channel layer 128 is higher by about two digits than that of $SiO_2$. For example, the thermal conductivity $\lambda$ of an undoped single crystal Si substrate is 148 W/(m·° C.), the thermal conductivity $\lambda$ of $SiO_2$ is 1.4 W/m·° C.), and the thermal conductivity $\lambda$ of $Si_3N_4$ is 25 W/(m·° C.). The thermal conductivity $\lambda$ of $Si_3N_4$ is changed by a manufacturing condition in a range of about 0.9 to 40 W/(m·° C.), and the thermal conductivity of the Si$_3$N$_4$ film can be designed by changing the film thickness thereof.

As illustrated in FIGS. 11A and 11B, a gate region 125 has a rectangular shape surrounded by the local oxidation film 40 and a PSG (phosphorus-doped glass) protective film 129, and the channel layer 128 is formed in the gate region 125 by way of a gate insulating film 25. The gate 20 is formed by sequentially forming a Ti film (having a thickness, for example, of 10 nm) and a Pt film (having a thickness, for example, of 5 nm) by an electron beam deposition method so as to ride over the edge of the local oxidation film 40 by a lift-off method. At this time, an air annealing treatment is performed at a temperature of 550° C. for one hour. The width of the gate 20 is designed so as to be larger by 3 μm than the gate length and, for example, to 8 μm.

The PSG protective film 129 for gate protection is formed over the n$^+$—Si layers 27S and 27D and the local oxidation film 40 except for the gate region 25 by a thermal CVD (Chemical Vapor Deposition) method. Further, a heater wiring 32 comprising WSi is formed over the PSG protective film 129. The thickness of the PSG protective film 129 is, for example, 300 nm. The heater wiring 32 has a thickness, for example, of 300 nm, a wire width, for example, of 1 μm, and a resistivity at a temperature of 150° C., for example, of 300 μΩcm. For example, the heater wiring 32 is formed between the gate 20 and the source electrode 21 in an accordion-fold shape comprising four wires each at a 1 μm interval based on the length unit of 30 μm, and the heater wiring 32 is also formed between the gate 20 and the drain electrode 22. In this case, the total length of the heater wiring 32 is about 250 μm. The resistance of the heater wiring 32 is, for example, 1.5 kΩ at a temperature of 150° C.

Over the heater wiring 32, a PSG protective film 130 is formed by a thermal CVD method. The thickness of the PSG protective film 130 is, for example, 300 nm. Further, in the PSG protective film 130, contact holes (for example, 3 μm square) 44H and 44S for connection to the heater wiring 32 and a contact hole (for example, 3 μm-square) 44G for connection to the gate 20 are formed. In the PSG protective films 129 and 130, contact holes 37 for connection to the n$^+$-type Si layers 27S and 27D are formed.

Further, a lead-out wiring 20H for connection to one end of the heater wiring 32 is formed via the contact hole 44H, a lead-out wiring 20S for connection to the other end of the heater wiring 32 is formed via the contact hole 44S, and a lead-out wiring 20G for connection to the gate electrode 20 is formed via the contact hole 44G. A source electrode 21 for connection to the n$^+$-type Si layer 27S and a lead-out wiring 20S are formed in the same layer, and a drain electrode 22 for connection to the n$^+$-type Si layer 27D and a lead-out wiring 20D are formed in the same layer. The lead-out wirings 20S, 20D, 20G, and 20H comprise Al formed, for example, by a sputtering method, and the thicknesses thereof is, for example, 500 nm. The lead-out wiring 20S is electrically connected to the other end of the heater wiring 32 via the contact hole 44S and to the source electrode 31S via the contact hole 37. The lead-out wirings 20S, 20D, 20G, and 20H are connected to pad electrodes 140, 41, 42, and 43 formed in the periphery of a sensor chip 45S, respectively.

Further, a final protective film 33 is formed over the lead-out wirings 20S, 20D, 20G and 20H, the source electrode 21, the drain electrode 22, etc. The final protective film 33 comprises, for example, a stacked film having a PSG film as a lower layer and an Si$_3$N$_4$ film as an upper layer. The PSG film of the lower layer is formed, for example, by a thermal CVD method and a thickness thereof is, for example, 200 nm. The Si$_3$N$_4$ film of the upper layer is formed, for example, by a low-temperature plasma CVD method and a thickness thereof is, for example, 1 μm.

The Si substrate 43a is bored as far as the filled insulation layer 123 in an MEMS region 34 (planar dimension, for example, of 200 μm×200 μm) in which a heater region 10, where the principal part of the heater wiring 32 is formed (planar dimension, for example, of 30 μm×24 μm) and an intrinsic FET region 35 where the principal part of the source electrode 21, the drain electrode 22, and the gate 20 of the sensor FET are formed (planar dimension, for example, of 44 μm×44 μm) are arranged. This structure is formed by a combined method of anisotropic dry etching and wet etching using a KOH solution. A threshold voltage of the sensor FET is designed, for example, to 1V. The threshold voltage of the sensor FET is defined by a gate voltage Vg which provides a source-drain current Ids=5 μA in a range of a drain voltage Vds=1.5 to 3 V.

Next, a structure in which the heat from the heater region 100 according to the first embodiment is adiabatically confined in the MEMS region 34 is to be explained.

In the case of the Si-MOS type gas sensor, 150° C. is an upper limit for the operation. When the set temperature (normal operation temperature) Ts of the heater region 100 is 150° C. in consideration of margin, it is required to increase the amount of heat generation (heater power Pow) generated by the heating of the flammable gas sensor in accordance with the lowering of the environmental temperature Te at which the flammable gas sensor is installed. The channel layer 128 and the n$^+$-type Si layers 27S and 27D comprising Si of excellent thermal conductivity exist below the heater wiring 32 in the intrinsic FET region 35, to provide an effect of improving the uniformity of the temperature by the heat generation from the heater wiring 32.

In the fifth embodiment, the heater regions 100 are arranged so as to interpose the gate 20 therebetween. Since the arrangement is extremely small, it can be considered that the temperature of the heater region 100 and the temperature of the gate 20 are substantially equal to each other. In consideration of the thermal diffusion from the heater region 100 to the environment where the flammable gas sensor is installed, assuming a thermal resistance between them as Rth, the temperature difference ΔT(=T−Te) at the temperature T of the heater region, the environmental temperature Te and the heater power Pow is expressed as:

$$\Delta T = Rth \times \text{Pow} \quad \text{formula (4)}$$

For the environmental temperature Te, when −35° C. is assumed as the lowest temperature of average installation environment, the temperature difference ΔT is 185° C. at the operation temperature of 150° C. In the first embodiment, the heater resistance is 1.5 kΩ at the operation temperature of 150° C. In consideration of the cell operation at 3 V, the heater maximum power Powmax is 6 mW and the temperature difference ΔTmax is 215° C.

Generally, the largest temperature difference ΔT is about 185° C., and the heater power Pow is 5.16 mW in the case of the continuous current supply. In consideration of heater control by the intermittent operation, continuous operation for one year or longer can be attached by using two lithium cells. The thermal capacity of the MEMS region 34 becomes about 1/10,000 of the thermal capacity (about 270 μW second/° C.) of the Si-MISFET-type gas sensor having the 2-mm-square sensor chip (thickness of the Si substrate: 0.4 mm) described above, for example, in the Non-Patent Literature 2. When the chip temperature is intended to be increased from the environmental temperature Te to the 150° C. upon power supply of 5.16 mW, the arrival time t0 can be shortened extremely to about 2.0 ms. Therefore, by the intermittent operation of turning on the heater wiring 32 (heating) for 6 seconds and turning off the heater wiring 32 (stopping of heating) for 24 seconds, the duty ratio can be decreased to ⅕, so that the effective consumption power of the flammable gas sensor can be reduced down to 1 mW without worsening the reliability of the detection performance of the flammable gas sensor. Thus, the operation for about one year can be achieved by using two lithium cells at a voltage of 3 V.

Further, the lead-out wirings 20S, 20D, 20G and 20H are formed of an Al film. The thermal conductivity λ of the Al film is 237 W/(m·° C.) as a metal material, which is decreased down to 180 W/(m·° C.) when formed as a tin film. The thermal conductivity of the WSi film is about 90 W/(m·° C.), and both of the films form a main thermal flow channels from the heater region 100. Therefore, improvement as explained below is required.

In the fifth embodiment, in order to thermally insulate the heat generation in the heater region 100 more effectively, a structure in which the sensor chip 45S is dominated by air which has outstandingly excellent heat insulation characteristics is adopted, by partially removing the PSG protective films 129 and 130 and the protective film 33, and further arranging the plurality of through-holes 36 penetrating through the filled insulation layer 123 in the region where the intrinsic FET region 35 does not overlap with the MEMS region 34. Since the relative distance between the intrinsic FET region 35 and the MEMS region 34 is 78 μm, air exists below the MEMS region 34, and a thermal conductivity λ of the air at 115° C. is as low as 0.03227 W/(m·° C.), the thermal insulation characteristics of this structure are excellent. However, if the through-holes 36 are excessively large, the mechanical strength of the MEMS region 34 is degraded. Meanwhile, although the protective film 33 comprising the Si₃N₄ film is required to protect the heater wiring 32 and the lead-out wirings 20S, 20D, 20G, and 20H, since it has the thermal conductivity which is about one digit higher than that of SiO₂, when the consumption power is reduced, the heat insulation characteristics of the bridge region where the lead-out wirings 20S, 20D, 20G and 20H are formed is not negligible.

Figure 11C:
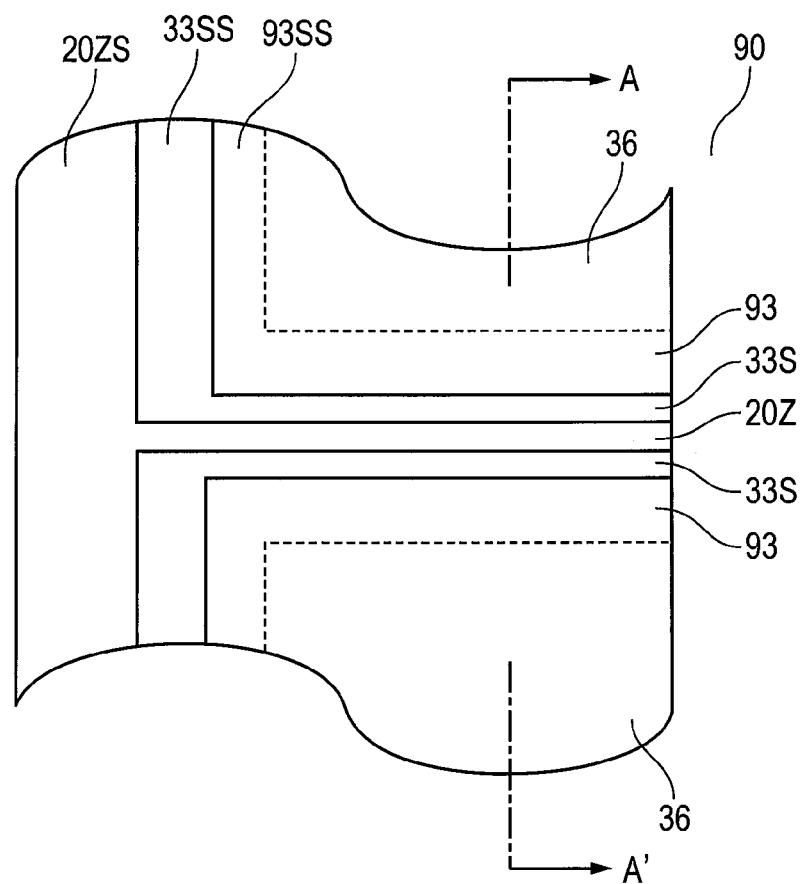
FIG. 11C is a planar view for a main portion enlarged for a portion of a bridge region formed in an MEMS region according to the fifth embodiment of the present invention.
Figure 11D:
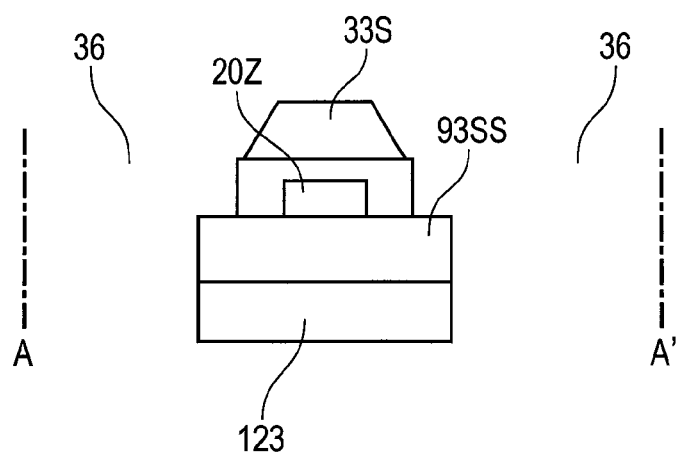
FIG. 11D is a cross sectional view of a main portion along line A-A' in FIG. 11C enlarged for a portion of a bridge region formed in an MEMS region according to the fifth embodiment of the present invention.

In consideration of the matters described above, a method of achieving the heat insulation is to be explained with reference to a plan view and a cross-sectional view illustrated in FIGS. 11C and 11D, respectively. FIG. 11C is an enlarged view of a peripheral portion of a bridge region 90 in FIG. 11B. The length of the bridge region 90 is, for example, 78 μm. The wire width of a lead-out wiring 20Z of the bridge region 90 is, for example, 2 μm, the wire width of a protective film 33S is, for example, 3 μm, a wire width of a stacked film 93 of the PSG protective films 129 and 130 is, for example, 6 μm. Further, in the peripheral portion of the intrinsic FET region 35, a relative distance between the lead-out wiring 20ZS and a protective film 33SS is, for example, 3 μm, and the relative distance between the protective film 33SS and a stacked film 93SS of the PSG protective films 129 and 130 is, for example, 3 μm. The structure is identical also in a bridge region 90G of the lead-out wiring 20G connected to the gate electrode 20, a bridge region 90H of the lead-out wiring 20H connected to one end of the heater wiring 32, and a bridge region 90S connected to the lead-out wiring 20S connected to the source electrode 31S and the other end of the heating wire 32. In order to reinforce the MEMS region 34, also the width of a reinforced region 91 where the stacked layer of the PSG protective films 129 and 130 is formed is, for example, 6 μm. When a distance between the edge of the MEMS region where the through-hole 36 is formed and the edge of the FET region is defined as a length of the bridge region 90, it is 78 μm in the fifth embodiment, which is the closest distance between the edge of the intrinsic FET region and the edge of the MEMS region. Accordingly, this is about 2.2 times the sum of the widths of all the bridge regions 90, 90S, 90G and 90H and the widths of all the reinforced regions 91 which is 36 μm (6 μm×6 wires), and it is usually formed as 1 to 20 times thereof.

In the bridge regions 90, 90S, 90G, and 90H, when it is assumed that the thickness of the Si₃N₄ film forming the protective film 33 is, for example, 1 μm that PSG is SiO₂, the PSG protective films 129 and 130 are formed to 3.8 μm based on SiO₂. Considering that the thermal conductivity of SiO₂ is 1.4 W/(m·° C.), the thermal conductivity of Si₃N₄ is 25 W/(m·° C.), the thermal conductivity of the Al thin film is 180 W/(m·° C.), and the thermal conductivity of the WSi thin film is 90 W/(m·° C.), the thermal resistance of the bridge region 90 is $9.1 \times 10^{4}$ ° C./W in three bridge portions concerned with the lead-out wirings 20S, 20D, and 20G, $39.65 \times 10^{4}$ ° C./W in one bridge portion concerned with the lead-out wiring 20H, and $12.22 \times 10^{4}$ ° C./W in two bridge portions concerned with the reinforced regions 91. These three thermal resistances are connected in parallel, so that the thermal resistance $R_M$ from the heater region 100 to the MEMS region becomes $4.61 \times 10^{4}$ ° C./W. In this case, thermal conduction due to the through-holes 36 is negligible.

Further, in view of the thermal conductivity of air of 0.03227 W/(m·° C.), the thermal resistance of a heat insulation material sandwiched between the sensor chip and the stem pedestal (reference symbol 50 in FIG. 12(a) to be described later) from the MEMS region 34 through the bored region in the MEMS region 34 to the front surface is estimated as $7.75 \times 10^{5}$ ° C./W. However, since it is higher by one digit or more than the thermal resistance $R_M$ of the heater region 100, this is negligible. That is, when the power of 5 mW is supplied to the heater region 100, the temperature difference between the bridge region and the heater region 100 becomes 230.5° C. ($=4.61 \times 10^{4}$ ° C./W×5 mW) and a sufficient heat-insulation effect can be expected.

On the other hand, since the thermal conductivity of the Si₃N₄ film forming the protective film 33 is higher by one digit or more than that of SiO₂, the film is removed while remaining a portion on the region where the intrinsic FET region 35 and the lead-out wirings 20S, 20D, 20G, and 20H are formed and the peripheral region of the bridge region described above. Further, a hatched portion of the lead-out wirings 20S, 20D, 20G, and 20H restricts the influence of the electric resistances of the lead-out wirings on the sensor FET, to increase the thermal resistance. Therefore it is designed, for example, by adopting a zigzag structure (which is not illustrated in FIG. 11B), etc. to a width, for example, of 10 μm and a length, for example, of 700 μm. In this case, the thermal resistance of the entire lead-out wirings is about $1.94 \times 10^{5}$ ° C./W. However, since the thermal conduction occurs through the Si substrate 22 having the high thermal conductivity except in the MEMS region 34, this less contributes to the thermal resistance $R_L$ in the MEMS system.

Figure 12:
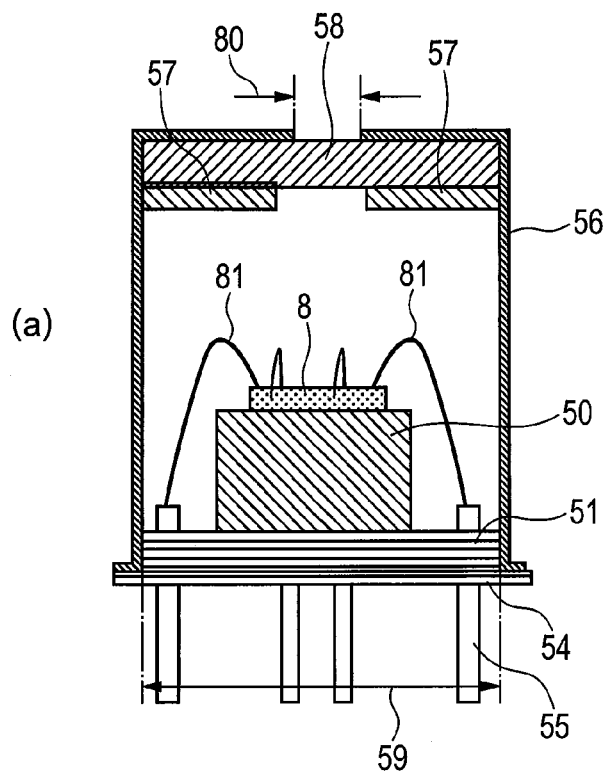
FIGS. 12 (a), (b), and (c) are a schematic cross sectional view of a gas sensor in which a sensor chip is mounted, a schematic rear face view of a stem base, and a schematic surface view of the stem base respectively according to the fifth embodiment of the present invention.
Figure 12:
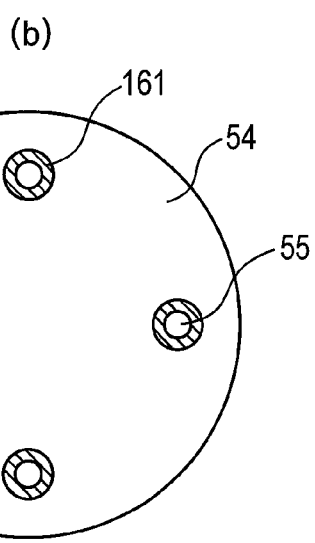
Figure 12:
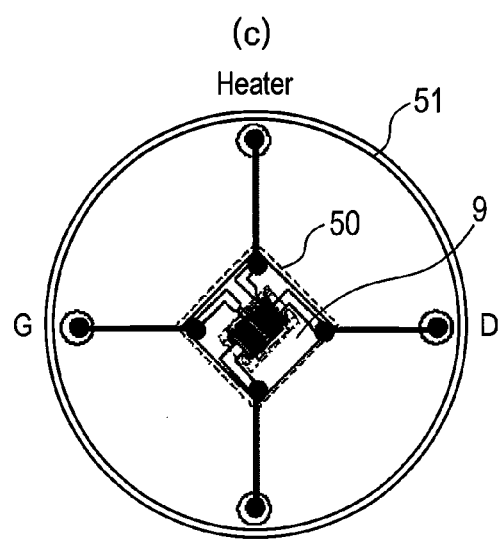

Next, description is to be made to a structure in which the heat from the heater region 100 according to the fifth embodiment is thermally insulated from the mounting substrate by the heat insulation material of the sensor chip. FIG. 12 is a view for explaining a basic configuration of a flammable gas sensor obtained by mounting the sensor chip according to the fifth embodiment on a stem having four lead terminals.

FIGS. 12(a), (b), and (c) are a cross-sectional view of the flammable gas sensor on which the sensor chip is mounted, a bottom view of a stem pedestal when the flammable gas sensor is viewed from a rearface thereof, and an upper plan view of the stem pedestal on which the sensor chip is mounted, respectively. Since the mounting shown in the fifth embodiment is a simple explosion-proof mounting, it is desired that the mounting portion is constructed by using commercialized products.

The mounting shown in the fifth embodiment is swaged from the inside thereof, for example, by using a PEEK (polyether ether ketone material) material 57 having a thickness of 3 mm. A cap 56 made of Kovar and a flange 54 of the stem pedestal are welded by a resistance welding method. As a water-proof moisture permeable material 58 used in the flammable gas sensor according to the first embodiment, a GORE-TEX (Registered Trademark) film formed by compositing a stretched film of polytetrafluoroethylene which is a typical fluorine resin with a polyurethane polymer. The water-proof moisture permeable material 58 has a feature of allowing moisture to permeate therethrough but not allow water to permeate therethrough (having both water-proof property and moisture permeable property together). In the example of the GORE-TEX film, the film contains 14 hundred millions of fine holes per 1 cm². A diameter of an air intake hole 60 is in a range of about 0.5 to 2 mm, but significant change of the hydrogen response has not been found. Although performances have been compared between ranges of 1 to 3 µm and 0.3 to 1 mm for the hole diameter and a thickness of the water-proof moisture permeable material 58, respectively, significant change could not been observed.

As the heat insulation material 50 formed on the 4-pin stem pedestal 51 comprising Kovar (inner diameter of the pedestal of 4.220, foamed glass (thermal conductivity of 0.061 W/(m·°C.)) is used, which is fabricated, for example, into a rectangular parallelepiped shape having a planar dimension of 0.6 mm×0.6 mm and a height of 3 mm, and is bonded to the stem pedestal 51. The thickness of the sensor chip 8 is, for example, 500 µm, and the planar dimension of the sensor chip 8 is, for example, 0.55 mm×0.55 mm. The height of a cap 56 is, for example, 12 mm, and the diameter of the air intake hole 80 is, for example, 1.5 mm. The hole diameter of the water-proof permeable material 58 is, for example, 1.0 µm, and the thickness thereof is, for example, 0.3 mm. The stem pedestal 51 has four lead terminals 55 penetrating through the stem pedestal 51 and protruding outside the front surface and the rear surface of the stem pedestal 51. The lead terminals 55 are fixed to the stem pedestal 51 by a glass material 161 provided in an outer circumference of the lead terminals 55. In FIG. 12(a), a dimension denoted by a reference symbol 59 is a cap size.

A lead wire (wire bonding) 8 is a gold wire, and has a diameter, for example, of 8 to 25 µm, and an overall length of 3 to 12 mm. Typically a lead wire comprising, for example, a gold wire having a diameter of 8µϕ and a length of 6 mm is used, and the above-described four pad electrodes 140, 41, 42, and 43 illustrated in FIG. 11B and the four lead terminals 55 are connected by the respective lead wires 8. A total thermal resistance $R_L$ of the four lead wires 8 is, for example, about $9.41 \times 10^{4 \circ}$ C./W. In this case, since the thermal resistance from the heater region 100 to the pad electrodes 140, 41, 42, and 43 is not included, it is considered that $9.41 \times 10^{4 \circ}$ C./W is the minimum value of the thermal resistance $R_L$. Further, a thermal resistance $R_D$ of the heat insulation material 50 in the MEMS region is $4.25 \times 10^{5 \circ}$ C./W. Further, the thermal resistance Rs of the heat insulation material 50 other than the MEMS region is $0.375 \times 10^{5 \circ}$ C./W.

Since the area of the heater region 100 is, for example, 30 µm×24 µm, a radius $r_A$ of a circle of this area is 15.1 µm, and $4\pi\lambda r_A$ is $0.613 \times 10^{-5 \circ}$ C./W by using the thermal conductivity λ (0.03227 W/(m·° C.)) of air at the temperature of 150° C.

Next, physical meanings of the above-described formulas (1) and (2) are to be explained with reference to FIG. 13A.

Figure 13:
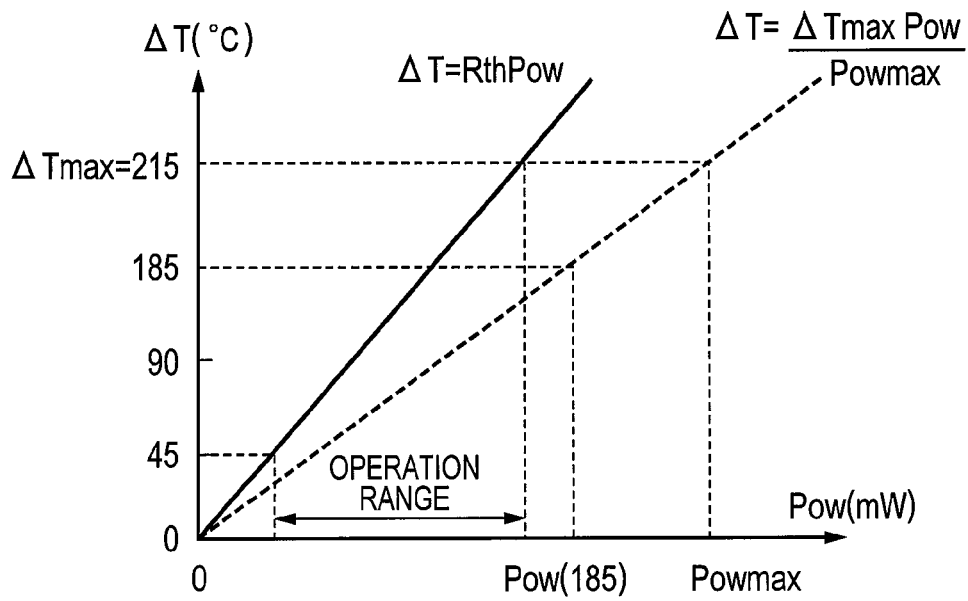
FIGS. 13 (a) and (b) are a graph explaining consumption power characteristics and a graph for explaining heater consumption power characteristics of a gas sensor, respectively, according to the fifth embodiment of the present invention.
Figure 13:
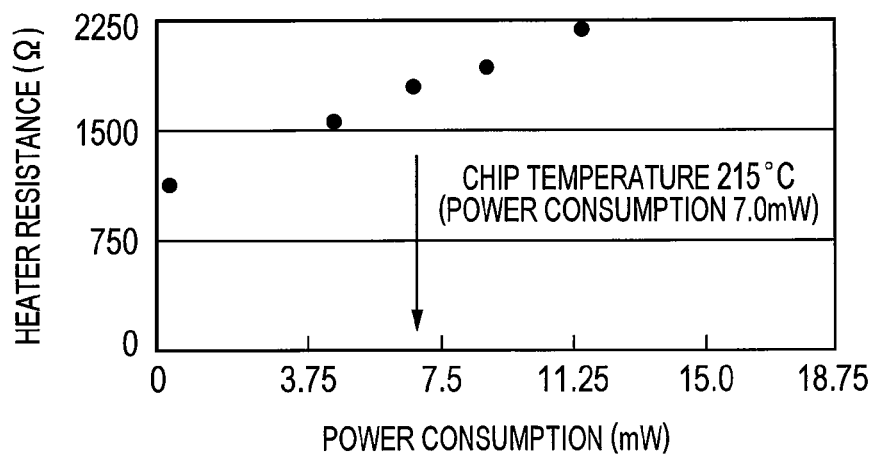

FIG. 13A is a graph for explaining a relationship of the temperature difference ΔT (=T−Te) between the operation temperature T of the gas sensor and the environmental temperature Te at which the gas sensor is installed and the heater power Pow charged to the heater wiring. The heater maximum power charged to the heater wiring determined by the electric resistance R(Ts) of the heater wiring at the set temperature Ts and the used power source voltage Vdd is represented as "Powmax".

In the case of the fifth embodiment, since Ts=150° C., R(TS)=1.5 kΩ and Vdd=3 V, the heater maximum power Powmax is 6 mW. Meanwhile, since Temin=−65° C. and Ts=150° C., the temperature difference ΔTmax(=Ts−Temin) is 215° C. between the set temperature Ts of the heater region and the environmentally-assumed lowest temperature Temin at which the flammable gas sensor is installed. A relationship between the temperature difference ΔT and the heater power Pow whose slope is the thermal resistance ΔTmax/Powmax is shown by a dotted straight line in FIG. 13A.

A relationship between the temperature difference ΔT of the gas sensor and the heater power Pow according to the fifth embodiment is shown by a solid straight line in FIG. 13A. The thermal resistance Rth is higher than the thermal resistance ΔTmax/Powmax, and satisfies the following relationship.

$$Rth > \Delta Tmax/Powmax \qquad \text{formula (5)}$$

This indicates that the gas sensor can be always operated by the consumption power of the heater maximum power Powmax or lower within a range between the temperature difference $\Delta T_{max}=215°$ C. at the lowest assumed external environmental temperature −65° C. and the temperature difference ΔT=45° C. at the highest environmental temperature 105° C. It is found that, at 25° C. (temperature difference ΔT=125° C.) which is a normal environmental temperature, the consumption power can be 0.58 compared with that of the temperature difference ΔTmax=215° C., and only the consumption power of 3.5 mW may be required even in Rth=ΔTmax/Powmax which is the lowest thermal resistance.

That is, when the formula (5) is satisfied, FIG. 13A shows that a temperature difference ΔT within a desired range can be always achieved by the consumption power of the heater maximum power Powmax or lower. A required condition for satisfying the formula (5) is the above-described formula (3), and all elements on the right of the formula (3) are measurable amounts, and elements on the left thereof are amounts determined from the operation specification of the gas sensor.

In the case of the operation at the sensor temperature of 150° C. which is the condition used in the fifth embodiment, the heater power Pow (185) corresponding to the temperature difference ΔT=185° C. determined from the thermal resistance ΔTmax/Powmax in the range between the temperature difference ΔTmax=215° C. at the lowest environmental temperature of −65° C. and the temperature difference ΔT=45° C. at the highest environmental temperature of 105° C. is 5.16 mW in the fifth embodiment.

As described above, in the gas sensor illustrated in the fifth embodiment, since $1/R_D=0.235\times10^{-5}$ W/° C., $1/R_P=0.137\times10^{-5}$ W/° C., and $4\pi\lambda r_A=0.613\times10^{-5}$ W/° C., Powmax/ΔTmax on the left of the formula (3) is $3.333\times10^{-5}$ W/° C., which satisfies the formula (3).

That is, by adopting the MEMS structure described above, when the sensor is operated at 150° C. under the environment of −35° C., the heat insulating performance can be ensured and the consumption power is reduced to about 5.18 mW and reduction of the consumption power to 1/100 or less is achieved compared with the case before applying the MEMS structure, and low consumption power that cannot be achieved by the bulk sensor or the thick film sensor in continuous current supply can be achieved. FIG. 13B illustrates a graph explaining a relation between the resistance of the heater wiring and the consumption power when a current is charged to the heater wiring while operating the gas sensor mounted as described above at 215° C. under the environment at an external temperature of −35° C. The resistance of the heater wiring is 1.7 kΩ and the consumption power is about 7 mW. Also in this case, the temperature difference between the heater region and the end of the MEMS region is about 120° C. and the temperature of surrounding Si is about 95° C. at the highest to achieve sufficient heat insulating characteristics. While description has been made in this embodiment to a case of using the gas sensor of the first embodiment to the MEMS region, it will be apparent that the gas sensor of the second embodiment can also be used to the MEMS region.

As described above, the present invention has been described with reference to the first embodiment to the fifth embodiment and the effects of the invention are summarized as shown below.

(1) A gas sensor capable of sensing various gases can be provided by applying a nano-scaled composite thin film in which a metal compound (nano compound) is formed in the platinum grain boundary nano space of the hyper thin film to a sensitive film of the gas sensor and changing the constituent metals of platinum and the nano compound, the film thickness, the occupancy ratio, and forming conditions. Particularly, a hyper thin film gas sensor of high long-term reliability and a method of manufacturing the same can be provided.

(2) A hyper thin film gas sensor capable of achieving reading of the amount of charges accumulated in the electric capacitance as a voltage signal upon deposition of adsorbed gas molecules in the electric capacitance between the hyper thin film platinum grains and the nano metal compound, as well as a method of manufacturing the same are provided by the provision of the nano-scaled composite thin film capable of controlling the occupancy ratio of the hyper thin film platinum grains and the nano metal compound.

(3) A hyper thin film gas sensor, capable of achieving reading of the change of the electric resistance of the nano-scaled composite thin film upon deposition of absorbed gas molecules to the nano metal compound as the change of the flowing current, change of the voltage, or change of the resistance as well as a method of manufacturing the same are provided by the provision of the nano-scaled composite thin film of further increasing the occupancy ratio of a nano metal compound compared with the hyper thin film platinum grains or having a nano metal compound in which conductive carriers are present.

(4) A hyper thin film gas sensor of high long-term reliability and a method of, manufacturing the same can be provided in the present application by forming an underlayer film of the nano-scaled composite thin film with a thin film containing a metal compound that forms the nano-scaled composite thin film.

(5) A hydrogen sensor operating at several hundred ppm or less and down to about several ppm and a hydrogen sensor operating in a concentration region from several % or more to several tens % in the Pt—Ti—O gate structure can be provided.

(6) A gas sensor in which the nano-scaled composite thin film or the underlayer film is formed over a semiconductor substrate such as of SiC, GaN, GaAs, etc. or over a glass substrate, as well as a method of manufacturing the same can be provided.

(7) In the sensor structure to achieve the purpose described above, a heat insulating structure capable of reducing the consumption power to about 1/100 or less and decreasing the temperature of the sensor substrate to 125° C. or lower in the portion other than the sensor portion could be provided by applying the MEMS structure compared with the case before application.

The invention made by the present inventors have been described specifically with reference to the preferred embodiments but it will be apparent that the present invention is not restricted to the embodiments and may be modified variously within a range not departing the gist thereof. A group of gas sensors can also be manufactured by using nitrides instead of the metal compounds formed in the grain boundary of the catalyst metal such as Pt, while the conditions of forming them are different.

INDUSTRIAL APPLICABILITY

The present invention can be utilized generally in the manufacturing industry of manufacturing the gas sensors formed by using semiconductor materials.

LIST OF REFERENCE SIGNS

1 adsorbed polar molecule
2 Ti mixed layer or Sn mixed layer
2a titanium oxide small crystal or tin oxide small crystal
2b oxygen-doped titanium film or oxygen-doped tin film
2c titanium oxide small crystal or tin oxide small crystal
3, 3a platinum small crystal
4 silicon oxide film
5, 5a, 28 Si semiconductor substrate
6, 6a, 14 depletion, layer in air
7 metal compound ($TiO_x$, $SnO_x$, etc.) nanostructure
7a air gap of Pt grain
77 crystal grain boundary
77a region near grain boundary
8 sensor chip
88 titanium oxide film
9 overlap between platinum grains to each other
10, 10a, 16, 16a depletion layer in reducing gas atmosphere
11 average distance between platinum grains
12 indication for specified gate position
13 Fermi level
15, 15a depletion layer in oxidizing gas atmosphere
16 air intake port
19 channel region
20 gate electrode
20a stacked film
20b thin film
20Z bridge region lead wiring
20ZS lead wiring
21, 21a source electrode
21a, 22a, 20D, 20G, 20H, 20S lead wiring
22, 22a drain electrode
23 SiN/PSG insulating film
24 PSG insulating film
25 gate insulating film ($SiO_2$ layer)
26 local isolation region
26a local isolation region
27 source region
27a drain region
27S, 27D $n^+$—Si layer
28 semiconductor substrate
29 substrate electrode
31S source electrode 32 heater wiring
33, 33S, 33SS protective film
34 MEMS region
35 intrinsic FET region
36 through hole
37 contact hole
40 local isolation region
41, 42, 43 pad electrode
41 p-type well
43, 43a n-type Si semiconductor substrate
44 p-type well electrode
44G, 44H, 44S contact hole
45S sensor chip
45 n$^+$-type semiconductor region
46 wiring
50 heat insulating material
51 stem pedestal
54 flange of stem pedestal
55 lead terminal
56 cap
57 PEEK material
58 water proof moisture permeable material
59 cap size
60 sensor FET
61 reference FET
63 heater
62 pn-junction diode
70 SOL film
80 air intake hole
81 lead wire
90, 90S, 90G, 90H, 95, 96 bridge region
91 reinforcing region
93, 93SS stacked film
100 sensor region
123 field insulating layer (SiO$_2$ layer)
125 gate region
128 channel region (Si layer)
129, 130 PSG protective film
140 pad electrode
161 glass material
221 molybdenum silicide film
440 local oxide film (SiO$_2$ film)
441 p$^+$-type semiconductor region
CHP semiconductor chip
Vth threshold voltage
ΔVg hydrogen response intensity
Vgs gate voltage
Id source drain current

The invention claimed is:

1. A gas sensor comprising:
(a) an insulating film disposed over a substrate, and
(b) an electrode disposed over the insulating film in which electric changes are detected that are caused by a gas molecule to be detected that is adsorbed on the electrode, wherein the electrode has:
(b1) a metal oxide mixed film where an oxygen doped amorphous metal and metal oxide crystals are mixed; and
(b2) a platinum film disposed over the metal oxide mixed film,
the platinum film comprises a plurality of platinum crystal grains and a grain boundary region present between the platinum crystal grains, and
the grain boundary region is filled with the metal oxide mixture film, and a periphery of the platinum crystal grains is surrounded by a structure formed by the metal oxide crystals that has an average width of at least 1 nm, and
wherein the platinum crystal grains are primarily connected by capacitive coupling or by resistance coupling.

2. The gas sensor according to claim 1, wherein
the substrate is a semiconductor substrate, and
the semiconductor substrate is provided with a source region and a drain region disposed such that one end of the source region is under one end of the electrode and one end of the drain region is under another end of the electrode.

3. The gas sensor according to claim 1, wherein
the electrode is provided with multiple lead electrodes.

4. A gas sensor having a capacitance element comprising:
(a) lower electrode comprising a semiconductor substrate,
(b) a capacitive insulating film formed over the lower electrode, and
(c) an upper electrode formed over the capacitive insulation film in which
electric changes, which are caused by a gas molecule to be detected that is adsorbed on the upper electrode, are detected by way of the gate insulating film, wherein
the upper electrode has:
(c1) a metal oxide mixed film where an oxygen-doped amorphous metal and metal oxide crystals are mixed, and
(c2) a platinum film disposed over the metal oxide mixed film,
the platinum film comprises a plurality of platinum crystal grains and a grain boundary region present between each of the platinum crystal grains, and
the grain boundary region is filled with the metal oxide mixture film, and a periphery of the platinum crystal grains is surrounded by a structure formed by the metal oxide crystals that has an average width of at least 1 nm, and
wherein the platinum crystal grains are primarily connected by capacitive coupling or by resistance coupling.

5. The gas sensor according to claim 1, wherein
the metal oxide mixed film is a titanium oxide mixed film in which oxygen-doped titanium or oxygen-doped amorphous titanium, and amorphous titanium oxide or titanium oxide small crystals are mixed together.

6. The gas sensor according to claim 1, wherein
the metal oxide mixed film is a tin oxide mixed film in which oxygen-doped tin or oxygen-doped amorphous tin, and amorphous tin oxide or tin oxide small crystals are mixed together.

7. The gas sensor according to claim 1, wherein
the amount of oxygen doped into the oxygen-doped amorphous metal is $10^{21}$ N/cm$^3$ or more and less than a solid solution limit.

8. The gas sensor according to claim 1, wherein
the average inter-grain distance of the platinum crystal grains is within a range from 1 nm to 10 nm.

9. The gas sensor according to claim 1, wherein
the platinum crystal grains are formed such that conductive carriers are present in the metal oxide mixed film.

10. The gas sensor according to claim 5, wherein
the thickness of the platinum film is 30 nm or more and 50 nm or less, and
the thickness of the oxygen-doped titanium film is 1 nm or more and 10 nm or less.

11. The gas sensor according to claim 1, wherein
the oxygen-doped amorphous metal is formed of indium (In), iron (Fe), cobalt (Co), tungsten (W), a molybdenum (Mo) film, a tantalum (Ta) film, a niobium (Nb) film, chromium (Cr), or nickel (Ni).

12. The gas sensor according to claim 1, wherein a heater for heating the gas sensor is further disposed over the semiconductor substrate.

13. The gas sensor according to claim 12, wherein
the sensor has a leading electrode in connection with the source region or the drain region,
the leading electrode comprises a stacked film where a gold film/molybdenum film are stacked in this order from the upper layer, and
the heater for heating gas sensor is formed of a stacked film comprising molybdenum film/metal film/molybdenum film.

14. A gas sensor including a sensor chip where an MOS structure gas sensor and a heater are formed on the main surface of a substrate, a mounting substrate for mounting the sensor chip, and a heat insulating material interposed between the sensor chip and the mounting substrate, wherein the sensor chip has:
an MEMS region formed by boring the rear side of the substrate,
a heater region having the heater formed therein and formed on the side of the surface of a substrate over the MEMS region, and
pad electrodes formed on the surface of the substrate and connected by way of the lead wiring to the heater, and
the mounting substrate has:
lead terminals penetrating the mounting substrate and used for connection with the outside, and
lead wirings for connecting the pad electrodes and the lead terminals in which,
a thermal resistance $R_P$ from the heater region through the edge of the MEMS region to the mounting substrate is represented as:

$$R_P = R_M + R_S \cdot R_L / (R_S + R_L),$$

where
$R_D$ represents a thermal resistance from the heater region through a bored cavity in the MEMS region to the mounting substrate that sandwiches the heat insulating material relative to the sensor chip,
$R_M$ represents a thermal resistance from the heater region to the edge of the MEMS region,
$R_S$ represents a thermal resistance from the edge of the MEMS region through the silicon substrate and from the heat insulating material to the mounting substrate, and
$R_L$ represents a thermal resistance for the sum of a thermal resistance from the heater region to the pad electrode and a thermal resistance of the lead wire, and
the thermal resistances $R_D$, $R_P$ and the surface area of the heater region are defined so as to satisfy:

$$\text{Powmax}/\Delta T\text{max} > 1/R_D + 1/R_P + 4\pi\lambda \cdot r_A$$

where
$R_D$ represents a thermal resistance from the heater region through the sensor chip and a bored a cavity in the MEMS region to the mounting substrate that sandwiches the heat insulating material relative to the sensor chip,
$r_A$ represents a radius of a circle having an area identical with the surface area of the heater region,
$\lambda$ represents a thermal conductivity of an atmospheric gas due to the heating of the heater,
$\Delta T\text{max}$ represents a difference between a set temperature of the heater region and an assumed environmental lowest temperature for installation, and
Powmax represents a heater maximum power charged to the heater which is determined by an electric resistance of the heater and a power source voltage at the set temperature, when the heater maximum power is 25 mW or less.

* * * * *